(12) United States Patent
Fischer et al.

(10) Patent No.: US 9,918,772 B2
(45) Date of Patent: Mar. 20, 2018

(54) ABLATION APPLICATOR WITH A MATRIX FILLED WITH PARTICLES

(75) Inventors: Gerald Fischer, Völs (AT); Florian Hintringer, Ampass (AT); Adrian Schütte, Aachen (DE); Michael Emonts, Aachen (DE)

(73) Assignee: Afreeze GmbH, Innsbruck (AT)

( * ) Notice: Subject to any disclaimer, the term of this patent is extended or adjusted under 35 U.S.C. 154(b) by 258 days.

(21) Appl. No.: 14/232,886

(22) PCT Filed: Jul. 13, 2012

(86) PCT No.: PCT/EP2012/063847
§ 371 (c)(1),
(2), (4) Date: Apr. 21, 2014

(87) PCT Pub. No.: WO2013/007831
PCT Pub. Date: Jan. 17, 2013

(65) Prior Publication Data
US 2014/0228831 A1 Aug. 14, 2014

(30) Foreign Application Priority Data
Jul. 14, 2011 (EP) .................................... 11174062

(51) Int. Cl.
*A61B 18/02* (2006.01)
*A61B 18/00* (2006.01)
(Continued)

(52) U.S. Cl.
CPC .......... *A61B 18/02* (2013.01); *A61B 18/1492* (2013.01); *A61B 18/20* (2013.01);
(Continued)

(58) Field of Classification Search
CPC .......... A61B 2018/00023; A61B 2018/00059; A61B 2018/00095; A61B 2018/0212; A61B 2018/0262; A61B 18/02
See application file for complete search history.

(56) References Cited

U.S. PATENT DOCUMENTS 4,314,559 A * 2/1982 Allen ..................... A61B 18/14
30/140
5,281,213 A 1/1994 Milder et al.
(Continued)

FOREIGN PATENT DOCUMENTS

EP 1 389 447 A1 2/2003
EP 1 356 779 A1 10/2003
(Continued)

OTHER PUBLICATIONS

International Preliminary Report on Patentability and Written Opinion of corresponding PCT/EP2012/063847, dated Jan. 23, 2014, 9 pages.
(Continued)

*Primary Examiner* — Ronald Hupczey, Jr.
*Assistant Examiner* — Bo Ouyang
(74) *Attorney, Agent, or Firm* — Lewis Roca Rothgerber Christie LLP

(57) ABSTRACT

An ablation applicator for an ablation device, the ablation applicator comprising a tubular body defining an inner lumen to which an ablation medium is conductible, wherein the tubular body comprises a matrix accommodating a plurality of particles.

28 Claims, 10 Drawing Sheets

(51) Int. Cl.
*A61B 18/14* (2006.01)
*A61B 18/20* (2006.01)
*A61B 17/00* (2006.01)

(52) U.S. Cl.
CPC .............. *A61B 2017/00292* (2013.01); *A61B 2018/00095* (2013.01); *A61B 2018/00101* (2013.01); *A61B 2018/00351* (2013.01); *A61B 2018/00357* (2013.01); *A61B 2018/00404* (2013.01); *A61B 2018/00577* (2013.01); *A61B 2018/00791* (2013.01); *A61B 2018/00994* (2013.01); *A61B 2018/0212* (2013.01); *A61B 2018/0262* (2013.01)

(56) References Cited

U.S. PATENT DOCUMENTS

| | | | |
|---|---|---|---|
| 5,423,807 A | 6/1995 | Milder | |
| 5,901,783 A | 5/1999 | Dobak et al. | |
| 6,182,666 B1 | 2/2001 | Dobak | |
| 6,241,722 B1 | 6/2001 | Dobak | |
| 6,589,234 B2 | 7/2003 | Lalonde et al. | |
| 6,602,247 B2 | 8/2003 | Lalonde | |
| 6,629,417 B2 | 10/2003 | Haas et al. | |
| 6,979,331 B2 | 12/2005 | Hintringer et al. | |
| 2002/0052613 A1* | 5/2002 | Ferrera | A61B 17/12022 606/157 |
| 2003/0036749 A1* | 2/2003 | Durkin | A61B 18/203 606/3 |
| 2006/0106298 A1* | 5/2006 | Ahmed | A61B 5/0422 600/381 |
| 2007/0123848 A1* | 5/2007 | Rioux | A61B 18/1477 606/41 |
| 2008/0312644 A1* | 12/2008 | Fourkas | A61B 18/02 606/22 |
| 2009/0287201 A1* | 11/2009 | Lalonde | A61B 18/02 606/21 |
| 2010/0081577 A1* | 4/2010 | Sidhu | B01J 19/0046 506/7 |
| 2010/0100087 A1* | 4/2010 | Mazzone | A61B 18/02 606/21 |
| 2010/0274178 A1* | 10/2010 | LePivert | A61B 18/02 604/21 |

FOREIGN PATENT DOCUMENTS

| | | | |
|---|---|---|---|
| EP | 1389447 | * 2/2004 | .............. A61B 18/00 |
| EP | 1 430 849 A1 | 6/2004 | |
| EP | 2 260 778 A1 | 12/2010 | |
| EP | 2260778 | * 12/2010 | .............. A61B 18/02 |
| GB | 2 236 253 A | 4/1991 | |
| WO | WO 00/32126 A1 | 6/2000 | |
| WO | WO 01/87379 A2 | 11/2001 | |
| WO | WO 03/037202 A1 | 5/2003 | |
| WO | WO 2006/009580 A2 | 1/2006 | |
| WO | WO 2008/099380 A2 | 8/2008 | |
| WO | WO 2008/157042 A1 | 12/2008 | |
| WO | WO 2009/112269 A2 | 9/2009 | |
| WO | WO 2009/137924 A1 | 11/2009 | |

OTHER PUBLICATIONS

Notice of Acceptance issued in parallel Australian Application No. 2012282473 dated Feb. 6, 2017, 3 pages.

Office action is parallel European Application No. 12 737 266.2 dated Jan. 19, 2017, 4 pages.

International Search Report and Written Opinion of PCT/EP2012/063847 dated Oct. 23, 2012, 14 pages.

* cited by examiner

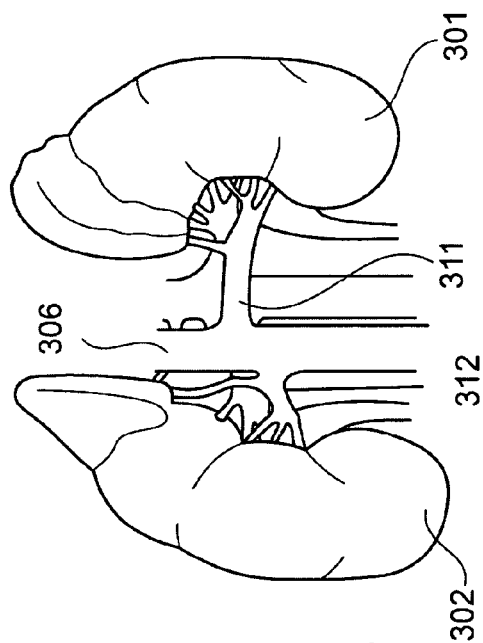
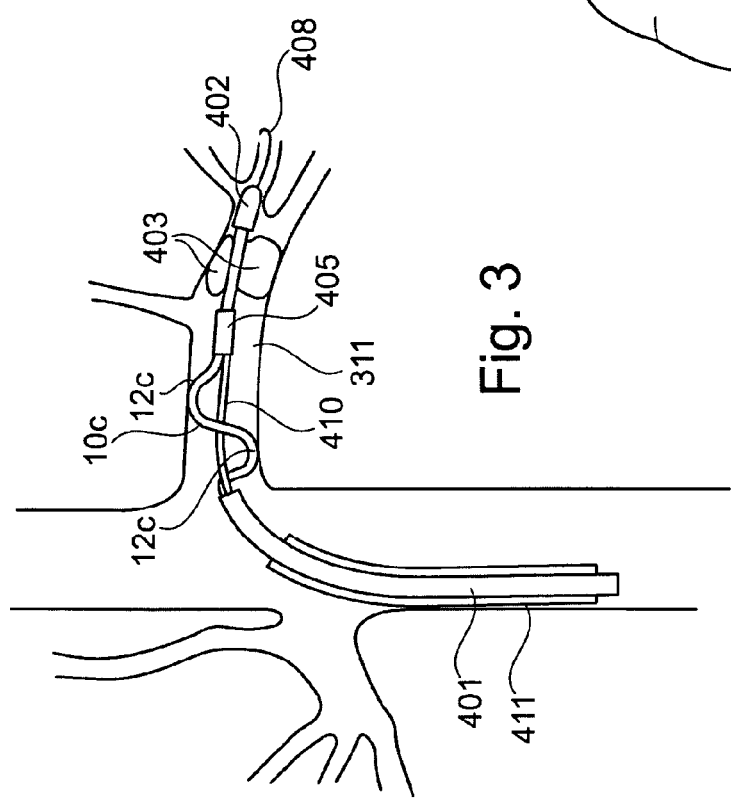
Fig. 3
Fig. 4

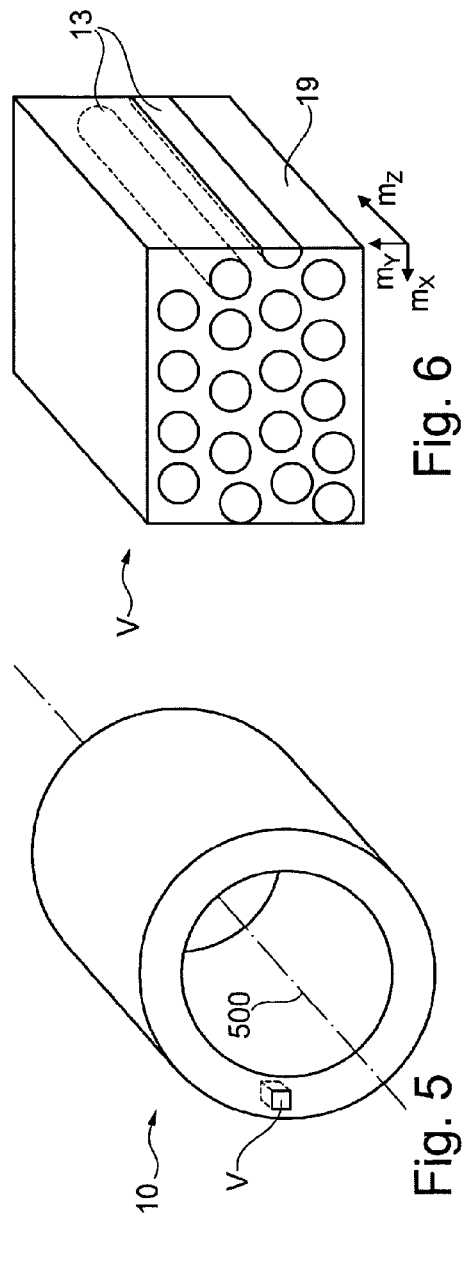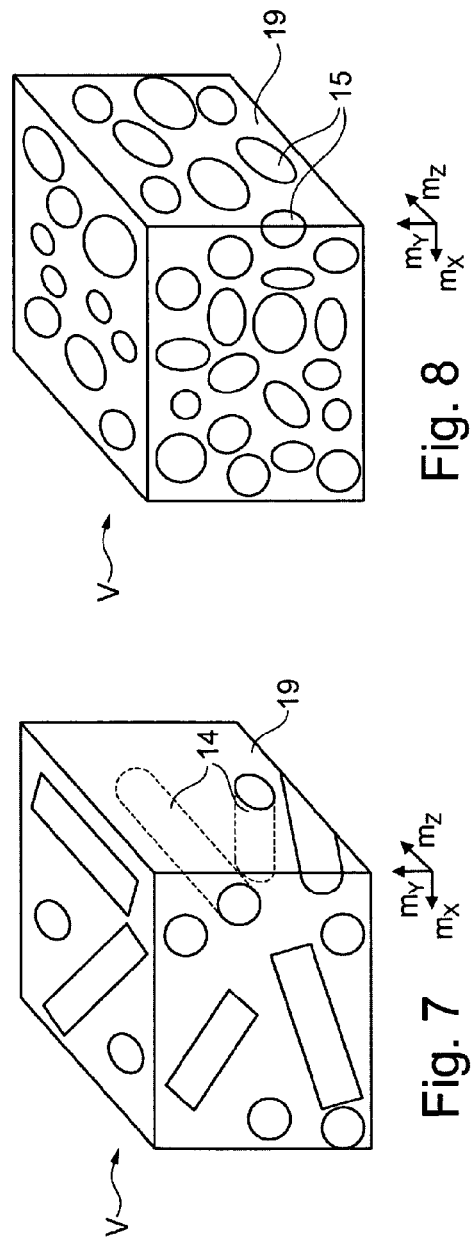

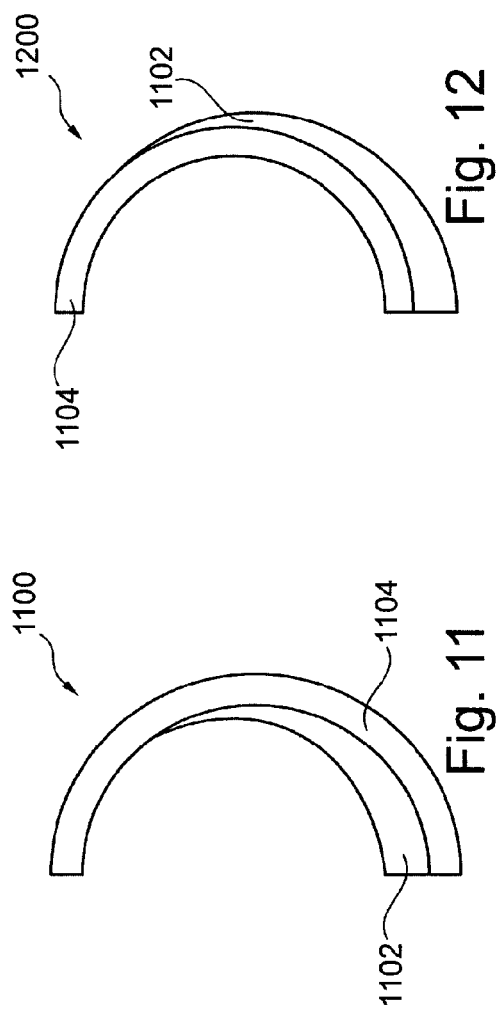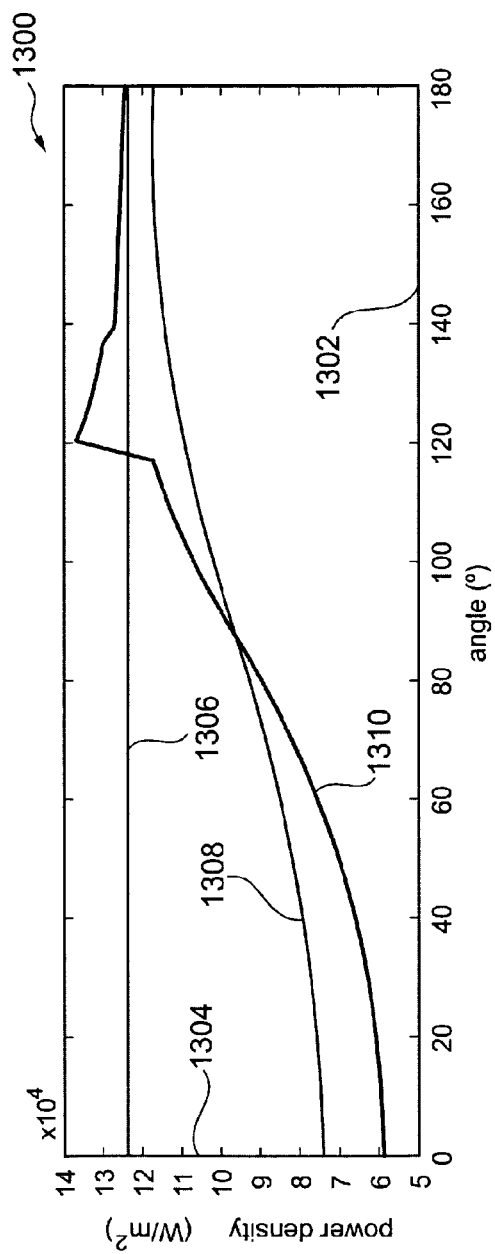

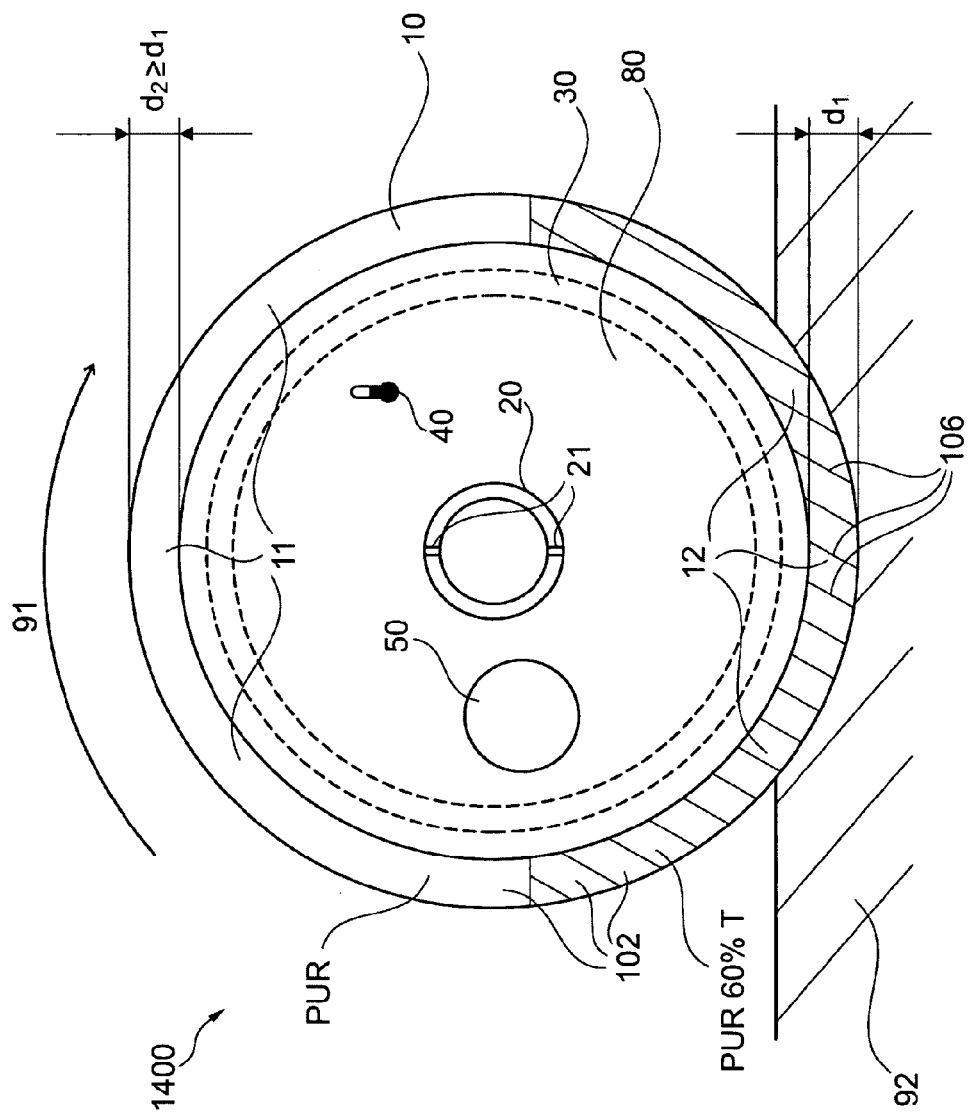

ABLATION APPLICATOR WITH A MATRIX FILLED WITH PARTICLES

CROSS-REFERENCE TO RELATED APPLICATION(S)

This is a National Phase Patent Application and claims priority to and the benefit of International Application No. PCT/EP2012/063847, filed on Jul. 13, 2012, which claims priority to and the benefit of European Patent Application No. 11174062.7, filed on Jul. 14, 2011, the disclosures of which are hereby incorporated by reference in their entireties.

FIELD OF THE INVENTION

The invention relates to ablation applicators.
Moreover, the invention relates to ablation devices.
Furthermore, the invention relates to ablation methods.

TECHNOLOGICAL BACKGROUND

In the field of cryoablation (therapeutic destruction of tissue by the application of extreme cold), a refrigerant vaporizes at low pressure and low temperature in a boiling chamber of an ablation catheter or a surgical probe. A thermally conductive structure forming a cryoapplicator allows the heat-exchange of the refrigerant with the tissue. Cryoablation, cryotherapy or cryosurgery are established treatments for the controlled destruction of tissue by the application of extreme cold. Examples for application are the removals of warts or moles, the destruction of tumor for the treatment of liver, prostate and lung cancer, and the selective ablation of cardiac tissue for the treatment of arrhythmia.

Rigid metallic structures are in widespread use for cryoapplicators, particularly if the target area is a spot or point like region. Here, U.S. Pat. No. 6,629,417 and U.S. Pat. No. 6,182,666 describe systems for the treatment of skin and endo-cervical tissue. Devices for the focal ablation of cardiac tissue are described in U.S. Pat. No. 5,281,213, U.S. Pat. No. 5,423,807 and U.S. Pat. No. 6,589,234. A system for cooling very small portions of tissue to extremely low temperatures is described in U.S. Pat. No. 5,901,783.

If tissue is ablated along an elongated region more flexible structures are used. Here, bellows surface can maintain both heat conduction and flexibility as described by U.S. Pat. No. 6,241,722. WO 00/32126 describes the combination of flexible segments with low thermal conduction with rigid segments of high thermal conduction. Here, also methods for the realization of a varying thermal conduction along the circumference of a cryoapplicator (good thermal conduction to the target tissue while limiting the heat loss on the opposite side of the applicator) are described. Furthermore, the use of thin walled tubing or inflatable balloon like material for the realization of good heat conduction in a flexible structure is described in U.S. Pat. No. 6,602,247 and EP 1,430,849.

One example which may require the creation of an elongated lesion in cardiac tissue is the treatment of atrial fibrillation. Here, a catheter design containing a loop like cryo-applicator structure is described in EP 1,356,779 and U.S. Pat. No. 6,979,331. Another example is the treatment of atrial flutter by creating an elongated lesion in the area of the cavotricuspid isthmus area as described in PCT/EP2009/001804.

Furthermore, WO 2009/112269 discloses an ablation element for an ablation device, the ablation element comprising a tubular body defining an inner lumen. The tubular body comprises a core formed by a wound filament structure and comprises a mantle surrounding the core. The tubular body, particularly the mantle, is configured to have a spatially varying value of thermal conductivity along a circumference of the tubular body.

However, although the arrangement of WO 2009/112269 already provides a proper solution for the spatially dependent supply of a cooling medium to tissue, there is still room for improvement.

SUMMARY OF THE INVENTION

There may be a need for an ablation applicator allowing for a spatially dependent supply of an ablation medium to surrounding tissue in an efficient way.

According to an exemplary embodiment, an ablation applicator for an ablation device is provided, the ablation applicator comprising a tubular body defining an inner lumen to which an ablation medium is conductible, wherein the tubular body comprises a matrix in (i.e. within and/or on) which a plurality of particles are accommodated (for instance are embedded in the matrix and/or are provided around the matrix).

According to another exemplary embodiment, an ablation device is provided which comprises an ablation catheter comprising an ablation applicator having the above mentioned features and being adapted to ablate physiological material, for instance material of a heart.

According to another exemplary embodiment, a method of configuring (or designing) an ablation applicator for an ablation device in accordance with at least one predefined ablation characteristic (for instance any target property which the ablation applicator to be designed should have in terms of ablating tissue) is provided, wherein the method comprises forming a tubular body defining an inner lumen to which an ablation medium is conductible and comprising a matrix in which a plurality of particles are accommodated, and selecting (for instance in terms of material selection, selection of geometrical parameters, selection of the density distribution of the particles in the matrix, etc.) the matrix and the particles so as to meet the at least one predefined ablation characteristic by the correspondingly configured ablation applicator.

According to another exemplary embodiment, an ablation method is provided, wherein the method comprises conducting an ablation medium to an inner lumen defined within a tubular body which comprises a matrix accommodating a plurality of particles, and ablating material by contacting the material with an external surface of the tubular body.

According to yet another exemplary embodiment, a cryoapplicator tubing is provided which is made from a polymer (as a matrix) being filled with particles in a first section (particularly a first circumferential section of the tubing) and being unfilled (i.e. being free of such particles) in another second section (particularly a second circumferential section of the tubing differing from the first circumferential section), wherein at least in one quarter (which may or may not be at least partially part of the first section or the second section) of a circumference of the cryoapplicator tubing, a heat transfer parameter is larger than 1500 W/m²K and at least in one other quarter (which may or may not be at least partially part of the first section or the second section) of the circumference the heat transfer parameter is smaller than 1200 W/m²K. Furthermore, an ablation device having a cryoapplicator with these features is provided as well.

According to an exemplary embodiment, an ablation applicator for an ablation device for ablating tissue of a blood vessel is provided, the ablation applicator comprising a tubular body defining an inner lumen to which an ablation medium is conductible, and a control mechanism configured for converting the tubular body between a passive operation mode (wherein "passive" is meant in terms of an ablation procedure, i.e. when no ablation is carried out; an example for a passive operation mode is an elongate operation mode) for inserting the ablation applicator into the blood vessel and an active operation mode (wherein "active" is meant in terms of an ablation procedure, i.e. when ablation is carried out or is about to be carried our; an example for an active operation mode is a spiral operation mode in which the tubular body assumes a spiral-shaped configuration; another example for an active operation mode is a spread operation mode in which the tubular body may expand laterally for contacting a wall of a blood vessel) for ablating tissue of the blood vessel, for instance along a helical path (alternatively, any other continuous or discontinuous ablation path is possible). Furthermore, an ablation device having an ablation applicator with these features is provided as well.

According to yet another exemplary embodiment, an ablation method of ablating tissue of a blood vessel (for instance a kidney blood vessel), particularly of an artery or a vein, more particularly along an inner surface of an artery or a vein, is provided, wherein the method comprises inserting a tubular body of an ablation applicator in a passive operation mode (wherein "passive" is meant in terms of an ablation procedure, i.e. when no ablation is carried out; an example for a passive operation mode is an elongate operation mode) into the blood vessel, converting the tubular body from the passive operation mode into an active operation mode (wherein "active" is meant in terms of an ablation procedure, i.e. when ablation is carried out or is about to be carried our; an example for an active operation mode is a spiral operation mode) when the tubular body is located at a target position in the blood vessel, and conducting an ablation medium to an inner lumen defined in the tubular body to thereby ablate tissue of the blood vessel, for instance along a helical path (alternatively, any other continuous or discontinuous ablation path is possible), when the tubular body is in the active operation mode.

In the context of this application, the term "ablation device" may particularly denote any apparatus which is adapted to ablate, deactivate, destroy or remove material, particularly tissue of a physiological object such as a human being or an animal, via the application of an ablation medium such as extreme cold provided by a cryoablation medium.

In the context of this application, the term "ablation applicator" may particularly denote a member or a part of an ablation device at which the actual tissue ablation is carried out, particularly by icing tissue. The ablation applicator may be part of a catheter.

In the context of this application, the term "tubular body" may particularly denote a body having an inner lumen of any desired internal and external shape. In a cross-section, the internal shape and/or external shape may be circular, oval, polygonal, etc. The tubular body may for instance have a round cross section, a square cross-section, etc.

In the context of this application, the term "ablation medium" may particularly denote a fluid, particularly a cryofluid such as $N_2O$, which is configured for providing cooling power for ablation tasks. Other possible ablation media are radio-frequency current, ultra-sound, laser, etc. An object to be ablated may particularly be a human being, an animal, or any plant (any organism). More particularly, it may be an organ of such a physiological object, particularly a heart or a part thereof, for instance the isthmus. It may be a living body so that living tissue may be investigated or processed.

In the context of this application, the term "lumen" may particularly denote a material free volume within the tubing through which an ablation medium such as a refrigerant may be guided so as to cool the tubular wall of the ablation applicator.

In the context of this application, the term "matrix" may particularly denote a support structure with a continuous material property in which individual particles are to be embedded. In other words, the matrix may form a continuum in which internal spaces are filled with the particles.

In the context of this application, the term "particle" may include any physical structure in solid, liquid or gaseous matter or even vacuum circumferentially surrounded by material of the matrix. Such particles may be basically spherical, may have a cuboid shape or may even have an elongated state. The particles may be made of electrically and/or thermally conductive, semi-conductive or insulating material, may provide mechanical stiffness or flexibility and may, if desired, also have shape-memory properties. A number of particles embedded in the matrix of the ablation applicator may be larger than 10, particularly larger than 100, more particularly larger than 1.000.

In the context of this application, the term "elongate" may particularly denote that in this configuration the ablation applicator may have an oblong appearance so as to be able to move along a narrow channel such as a blood vessel. This may be a completely straight orientation of the ablation applicator, but may also be a slightly bent ablation applicator.

In the context of this application, the term "heat transfer parameter" may particularly denote the value of a parameter being defined as a ratio between a thermal conductivity (particularly, for instance in case of anisotropic thermal conduction properties, along a direction across a wall of the tubing, i.e. between an interior surface and an exterior surface of the tubing) and a wall thickness of the respective portion of the tubing between an interior wall and an exterior wall of the tubing). In this context, the thermal conductivity may be measured by the laser flash method, as for instance performed by the ZAE Bayern. In the laser flash method, a surface of a sample is irradiated with a laser beam as a heat source, and heating of an opposing surface of the sample is measured in response to the laser heating. A mathematical analysis of the time dependence of the temperature allows to determine thermal conductivity of the sample.

In the context of this application, the term "spiral" may particularly denote a helical arrangement. Such a helical arrangement may be formed by windings which are sufficiently closed together (i.e. located next to one another) that, upon application of ablation power, the thermal conductivity is sufficient to provide for a basically uninterrupted or continuous ablation along a hollow cylindrical inner surface of the blood vessel.

According to a first aspect of the invention, a matrix material having embedded therein a definable amount, kind and local distribution of particles is provided for ablation purposes to make it possible to precisely adjust the properties of the ablation to a desired application. For instance, it may be advantageous for ablation applications to have a higher thermal conductivity at specific circumferential portions (for instance those directly contacting tissue to be ablated) of the ablation applicator as compared to other circumferential portions (for instance those directly contacting tissue not to be ablated). This may be advantageous so as to apply high ablation power to tissue to be ablated, whereas other tissue should be safely parented from being cooled to a too low temperature. By embedding particles in a hollow cylindrical matrix it is also possible to adjust any other desired physical properties apart from thermal conductivity such as electrical conductivity, mechanical flexibility or stiffness, shape memory behavior, etc.

According to a second exemplary aspect of the invention, an ablation catheter is provided which is specifically configured to apply ablation energy (such as apply a cooling power) to an interior (for example tubular or basically tubular) surface of a blood vessel, particularly of a kidney. For simultaneously allowing to insert such a catheter (for instance with a basically hollow cylindrical ablation surface) into a blood vessel, it is possible to convert the active (for instance helical) shape of the ablation applicator into a passive (for instance an elongated) state in which the radial extension may be significantly reduced as compared to the active (for instance expanded) ablation mode.

DETAILED DESCRIPTION OF EXEMPLARY EMBODIMENTS

In the following, further exemplary embodiment of the ablation applicators will be explained. However, these embodiments also apply to the ablation devices and the methods.

In an embodiment, the plurality of particles comprises fibers, particularly carbon fibers, glass fibers and/or nylon fibers. The term "fibers" may particularly denote elongated pieces of a given material, for instance roughly round or rectangular in cross-section and straight or bent perpendicular thereto, optionally twisted with other fibers. Fibers may be particles which have an aspect ratio which is larger than 2, particularly larger than 5, more particularly larger than 10. The aspect ratio is the ratio between the length of the fiber (when being in or when brought to a longitudinally extending state) and a diameter of the fiber. Fibers may form networks by being interconnected or interwoven. Fibers may have a substantially cylindrical form which may however be straight, bent, kinked, or curved. Fibers may consist of a single homogenous material and may hence be a non-composite material. Alternatively, fibers may be made of different materials.

In an embodiment, the plurality of particles is aligned relative to one another in an ordered structure. Examples of such an ordered arrangement are an alignment of all particles along the same direction, but also only an angularly differing (for instance distributed) orientation of different particles however still in accordance with a preferred direction ("Vorzugsrichtung"). For instance, the particles may be extruded fibers and may then have a lower degree of ordering. Ordering the particles allows for adjusting a spatially anisotropic physical property such a thermal and/or electrical conductivity. An ordered insertion of fibers into the matrix material may allow to adjust anisotropic properties. Examples for such ordered arrangements are a straight arrangement of fibers parallel to one another and to a main extension of a tubular ablation applicator. An ordered arrangement of fibers may also result from helically winding or wrapping them around a hollow matrix tube, wherein the windings may be parallel to one another.

In an embodiment, at least a part of the plurality of particles, particularly fibers, are aligned parallel to one another, particularly aligned parallel to a longitudinal axis of the tubular body (when being in or when brought to a longitudinally extending state). For instance, in such an embodiment, heat and/or an electrical current can be transported basically along the longitudinal extension of the fibers, but not with the same efficiency to a direction perpendicularly thereto. As an alternative to a longitudinal extension, it is also possible to have a defined fiber orientation not necessarily parallel to the longitudinal axis.

In an embodiment, at least a part of the plurality of particles, particularly fibers, is spirally wound, particularly around an exterior and/or an interior surface of the tubular body. Such an arrangement may, depending on the used particles, act as a heat bridge (for promoting the conduction of heat through a wall of the tubing) or as a heat barrier (for suppressing or inhibiting the conduction of heat) through a wall of the tubing). In another embodiment, at least a part of the plurality of particles, particularly fibers, may be braided, particularly around an exterior and/or an interior surface of the tubular body. The term "braiding" may particularly denote an interweaving or twinning of two, three or more separate fibers in a diagonally overlapping pattern. The fibers may be of one or more materials. Braids can be flat or tubular. A braiding, particularly a metal braiding, may be used to provide a high mechanical stability and at the same time a sufficient flexibility.

In an embodiment, at least a part of the plurality of particles, particularly fibers, is oriented in a non-ordered way, for instance statistically or stochastically within and/or on the matrix tube. Such an embodiment may ensure that the physical properties in a section with such an arbitrary orientation of the fibers occurs is homogeneous. Hence, it is also possible to arrange the fibers in an arbitrary orientation without any preferential alignment direction, thereby allowing to adjust isotropic properties of the ablation applicator, for instance in terms of thermal conductivity.

In an embodiment, the plurality of particles comprises beads, particularly tungsten beads, silver beads, gold beads and/or barium sulphate beads. Other examples for beads include ion or ion-oxide particles for MRI contrast, or also other contrast agents (such as gadolinium). The term "beads" may particularly denote particles being significantly less elongate than fibers, for instance having an aspect ratio smaller than two, particularly smaller than 1.5. Beads may have a spherical, cuboid or other shape. Different beads may have a homogeneous or inhomogeneous shape and/or size, and may have defined or distributed shapes and/or sizes. A basically spherical geometry of such beads may ensure a corresponding homogeneity of the respective physical parameters. A spatially anisotropic geometry of such beads may ensure a corresponding inhomogeneity of the respective physical parameters.

In an embodiment, the plurality of particles comprises nanowires. The term "nanowire" may denote a wire-like structure of dimensions in the order of magnitude of several to several hundreds of nanometers (and may also cover larger or smaller dimensions). Many different types of nanowires may be used for embodiments of the invention, including semiconducting nanowires (for instance made of silicon, germanium, InP, GaN, etc.), metallic nanowires (for instance nickel, platinum, gold), and nanotubes, particularly carbon nanotubes (intrinsic or doped). The nanowire may also be an isolating nanowire (in case the nanowire is covered by an isolation layer).

In an embodiment, at least about 50% (particularly at least about 80%, more particularly at least 90%) of the plurality of particles, when being configured as beads, in the matrix have a size in a largest dimension (in case of a spatially anisotropic geometry of the particles) in a range between about 100 nm and about 100 μm, more particularly in a range between about 500 nm and about 5 μm. For instance, an average diameter of tungsten beads may be 0.8 μm.

In an embodiment, at least about 50% (particularly at least about 80%, more particularly at least 90%) of the plurality of particles, when being configured as fibers, in the matrix have a size in a largest dimension (i.e. a longitudinal direction of the fibers) in a range between about 1 mm and about 10 m, more particularly in a range between about 1 cm and about 1 m. A diameter of such fibers may be in a range between about 1 μm and about 100 μm, more particularly in a range between about 5 μm and about 20 μm. Hence, the fibers may have an aspect ratio (length divided by diameter) being significantly larger than one.

In an embodiment, the matrix is a continuum which may be free of gas inclusions such as air bubbles. Such a configuration of the matrix material is technically highly appropriate, since it ensures at the same time a sufficient stability of the ablation applicator for simplifying insertion into a living body and at the same time providing for sufficient flexibility so that the ablation applicator, when being inserted, may be guided along and around anatomic obstacles without the danger to harm or injure tissue.

In another embodiment, the matrix is formed to include at least one gas inclusion such as an air bubble. By such an intentionally provided gas inclusion, it is possible to define poorly thermally conductive sections of the tubular body.

In an embodiment, the matrix is of a material with a Shore hardness in a range between about 50D and about 70D, particularly about 55D and about 65D. Thus, a quite hard plastic (such as polyurethane) may be used for the matrix.

In an embodiment, the particles and/or the matrix material is or comprises a shape-memory material. For instance, such a shape-memory material may be configured so as to assume an initially defined geometrical shape or orientation when being heated to a certain temperature. This temperature (Af, austenite finish) at which the shape memory material converts from an initial state to a final state in terms of geometrical properties can be selected in accordance with but lower than a body temperature of a human being, for instance may be in a range between 0° C. and 20° C. Hence, insertion of a corresponding ablation applicator into the human body may automatically result in the change of the shape of the ablation applicator from an oblong state suitable for insertion into a bent or wound configuration for ablation.

In another embodiment, the ablation applicator comprises a structure of a shape-memory material provided as a member being separate from the tubing (for instance may be arranged in the lumen or in a further separate recess formed in the tubing). In such an embodiment, the shape-memory material may be adjusted separately from a matrix material so that each of these materials may be adjusted specifically in accordance with its respective function. Again, the temperature (Af, austenite finish) at which the shape memory material converts from an initial state to a final state in terms of geometrical properties can be selected in accordance with but lower than a body temperature of a human being, for instance may be in a range between 0° C. and 20° C.

In an embodiment, the matrix is made of a synthetic material, particularly a synthetic polymer such as polyurethane or silicone. Such materials have the advantage to be biocompatible, light-weight, somewhat flexible and at the same time sufficiently rigid, and also have the chemical property to allow particles to be embedded therein without losing their continuous structure. However, other polymers (such as polyamide) are suitable for this purpose as well.

In an embodiment, the plurality of particles are included in the matrix with a varying composition along a circumference of the tubular body (such as a circular perimeter in case of a hollow cylindrical tubular body). For instance, if the particles are highly thermally conductive, a high concentration or accumulation of such particles may be set at a circumferential portion of the ablation applicator at which the actual ablation or lesion should be performed. In contrast to this, the concentration of these particles may be lower in other circumferential portions of the ablation applicator which should not be subject to ablation. Even more preferably, other particles with a poor thermal conductivity may be provided with a high density in such circumferential portions of the ablation applicator which should not be subject to ablation. Therefore, the adjustment of the concentration and/or the type of the particles along a circumference may allow adjusting the ablation properties such as the ablation trajectory.

In an embodiment, the plurality of particles are included in the matrix so that the tubular body has a circumferentially varying thermal conductivity. In one more specific embodiment, a first circumferential portion has first particles with a first thermal conductivity over a first angular range, and a second circumferential portion has second particles with a second thermal conductivity over a second angular range. At least one third circumferential portion may be free of particles (i.e. may consist of matrix material) over a third angular range. The first particles may differ from the second particles, and the first thermal conductivity may differ from the second conductivity. Any of the angular ranges may be between 45° and 180°, particularly between 60° and 135°. In an embodiment in which the second particles are omitted, any of the angular ranges may be between 90° and 240°. It goes without saying that the sum of the angular ranges around the entire circumference of the tubular body is always 360°.

Additionally or alternatively, the plurality of particles are included in the matrix so that the tubular body has a longitudinally varying thermal conductivity. This may advantageous for instance in an embodiment as shown in FIG. 15 to FIG. 17 in which a tip of a catheter shall be made better thermally conducting than a remote portion of the catheter which is equivalent to a longitudinal variation of the thermal conductivity.

In an embodiment, the plurality of particles are included in the matrix so that the tubular body has a thermal conductivity within at least a part of its circumference of more than 0.25 W/(mK), particularly of more than 0.30 W/(mK). In an embodiment, the tubular body has a thermal conductivity within at least a part of its circumference of less than or equal to 1 W/(mK). If the matrix material is a kind of plastic and the particles are of high thermal conduction (for example metal or carbon) conductivities up to 4 W/mK can be obtained in the direction across the wall of the tubing i.e. from the inner surface to the outer surface by a dense packing of the particles. It has turned out that these values of the thermal conductivity are highly advantageous to provide for a precise and defined ablation.

In an embodiment, a volume percentage of the fibers in the tubular body (i.e. a ratio between the volume of the fibers on the one hand and the volume of the matrix material plus the volume of the fibers on the other hand) is in a range between about 20 vol. % and about 80 vol. %, particularly in a range between about 40 vol. % and about 70 vol. %.

In another embodiment, a mass percentage of the beads in the tubular body (i.e. a ratio between the mass of the beads on the one hand and the mass of the matrix material plus the mass of the beads on the other hand) is in a range between about 20 mass % and about 80 mass %, particularly in a range between about 40 mass % and about 70 mass %.

At lower partial volumes/masses of the particles, the effect of the particles may become too weak for high performance ablation. At higher partial volumes/masses of the particles, it may become difficult to securely embed the particles in the matrix material.

In an embodiment, the tubular body comprises a first section in which a plurality of particles of a first type are included in the matrix, and comprises a second section in which a plurality of particles of a second type are included in the matrix. By providing two or more different types of particles having different physical properties, the spatial dependency of desired thermal, geometrical, mechanical and/or electrical properties can be further refined.

In an embodiment, the tubular body comprises a third section being free of particles. Also the provision of particles only in a certain portion along the circumference may already allow to adjust the properties of the ablation applicator in a spatially dependent manner, since in the particle free portion the properties are defined by the matrix material only.

In an embodiment, the particles of the first type are thermally conductive, and the particles of the second type are thermally insulating. Hence, the thermally conductive particles should be accumulated along a definable lesion trajectory, whereas the thermally insulating particles may be located in portions of the circumference of the tubing which shall not be subject to a lesion.

In an embodiment, the tubular body comprises a first section in which the plurality of particles are included in a matrix section of a first type (for instance in a first matrix material), and comprises a second section in which the plurality of particles are included in a matrix section of a second type (for instance in a second matrix material differing from the first matrix material). Hence two, three or even more different types of matrix materials may be used to form the tubing to fine-tune the properties of the ablation applicator.

In an embodiment, the particles have a core and a coating at least partially covering the core. For example, the material of the core (such as a sphere or a cylinder) may be configured or optimized with regard to the physical properties to be achieved, whereas the coating (such as a sphere shell or a hollow cylinder) may provide compatibility with the surrounding matrix material, for instance may be optimized with regard to adhesion to the matrix material.

In an embodiment, the tubular body has a closed end formed at least partially by the matrix and the particles. In other words, a for instance hollow cylindrical section of the tubular body may be closed at one end by a half shell. The closed end may for instance have a semi-spherical shape to prevent any injury when the ablation applicator is inserted into a human being.

In an embodiment, the ablation applicator comprises at least one electrically conductive structure at an exterior surface of the closed end and being connected to or integrally formed with the tubular body. Such an electrically conductive structure may be provided integrally with the matrix having the embedded particles (which may then have electrically conductive properties) or may be a separate component (such as a metal cap). The electrically conductive structure may function as an electrode, for instance a sensor electrode or may be used for other purposes (such as ablation) as well.

In an embodiment, at least a portion of the tubular body different from the closed end, particularly an entire remaining portion of the tubular body different from the closed end, may be made of a material being free of accommodated particles. By taking this measure, specifically the closed end may function as a tip-shaped ablation applicator. It is possible to configure the accommodated particles exclusively at this tip to be highly thermally conductive. In contrast to this, the rest of the tubular body may be significantly less thermally conductive and will therefore not contribute to the ablation. Optionally, the tip may be partially or completely constituted by a metallic portion.

In an embodiment, an outer circular perimeter of the tubular body and a circular perimeter of the lumen (i.e. an inner perimeter of the tubular body) are arranged to be eccentric (i.e. not concentric) in such a manner that a thickness of the tubular body varies along the circumference of the tubular body. By taking this measure, a further design parameter (i.e. local wall thickness) for adjusting thermal conductivity between the lumen and an exterior of the ablation applicator can be provided. Usually, the thicker the material the lower is the thermal coupling.

In an embodiment, a portion of the tubular body having a higher thickness than other portions of the tubular body is filled with particles in the form of fibers aligned along a longitudinal axis of the tubular body (when the latter is in or is brought to a straight configuration). Thus, the properties of the thickened portion may be further defined by filling this region with fibers extending along a different direction than the heat flow between an interior and an exterior of the tubing.

In an embodiment, an exterior surface of the tubular body is spirally wrapped with particles in the form of fibers. Thus, after having finished manufacture of the matrix, it is possible to wind the particles simply around the external surface of the matrix tube. By taking this measure, the wrapped portion may be rendered highly or poorly thermally conductive, depending on the material of the used fibers.

In an embodiment, a thickness of the tubular body at a thinnest circumferential position of the tubular body is smaller than about 0.20 mm, particularly not smaller than about 0.16 mm. A thickness of the tubular body at other circumferential positions of the tubular body may be larger. Such a small thickness may ensure proper thermal coupling between the lumen and an exterior of the ablation applicator, for instance by the filling with appropriate thermally conductive particles. At the same time, the thickness is sufficiently large to allow sufficient stability of the ablation applicator particularly during insertion and to provide a thermal decoupling between interior and exterior of the tubing by the filling with appropriate thermally insulating particles. In an embodiment, a thickness of the tubular body at a thickest circumferential position of the tubular body is smaller than about 0.35 mm, particularly not smaller than about 0.25 mm.

In an embodiment, the tubular body is formed by inserting the plurality of particles into the matrix by pultrusion. Pultrusion is a continuous process for manufacture of composite materials. Particles such as reinforced fibers are pulled through a resin or other matrix raw material, possibly followed by a separate preforming system, and into a heated die, where the resin undergoes polymerization or the other matrix raw material is hardened. This is a very simple procedure of manufacturing the matrix with the particles embedded therein. Other methods of providing ordered arrangements of particles being ordered relative to one another and/or relative to the matrix material are wrapping fibers around a matrix tube, magnetically aligning magnetic beads by applying a magnetic field, etc.

In an embodiment, the ablation applicator comprises an ablation medium supply line for supplying ablation medium, being arranged within the lumen and having a number of recesses (for instance twelve hole pairs, but it may even be a single hole) for conducting ablation medium from the ablation medium supply line to the lumen for thermally contacting the ablation medium with the tubular body. Thus, for instance a refrigerant such as $N_2O$ may be conducted from a reservoir through the ablation medium supply line or conduit. From there, it may flow through the recess or recesses, thereby expanding into a boiling chamber which may be a volume between the ablation medium supply line and the tubular body. The cooling power of the ablation medium may then impact the tubular body with its spatially dependent thermal conductivity properties, particularly circumferentially varying thermal conductivity properties. Hence, although the boiled ablation medium is supplied to a basically hollow cylindrical space between ablation medium supply line and the tubular body, an anisotropic transmission of the cooling power to tissue surrounding the tubular body may nevertheless be adjusted, thereby allowing to select which portions of the tissue are to be ablated and which not.

In an embodiment, the number of recesses comprises recesses arranged with a predetermined spacing in the longitudinal direction of the tubular body. The predetermined spacing may preferably be less than 8 mm or even less than 6 mm, thereby assuring that ablation medium is thermally contacting with a continuous section of the tubular body.

In an embodiment, the cross-sectional area of at least one proximal recess (a recess positioned towards the proximal end of the ablation applicator) is smaller than the cross-sectional area of at least one distal recess (a recess positioned towards the distal end of the ablation applicator). Thereby, pressure variations along the ablation medium supply line can be compensated, such that a uniform distribution of the ablation medium is achieved along the tubular body.

In an embodiment, at least two neighboring recesses (two recesses separated by the predetermined spacing) may have the same cross-sectional area. In particular, several groups of recesses may be arranged in the longitudinal direction of the tubular body, wherein the recesses of each group has the same cross-sectional area.

In an embodiment, the ablation applicator may further comprise a temperature sensor arranged within the inner lumen for monitoring the temperature therein. The temperature sensor may preferably be arranged in the vicinity of one of the recesses. A further temperature sensor may preferably be arranged in the vicinity of another one of the recesses. The temperature sensor is preferably arranged towards a proximal end of the lumen (i.e. in a proximal portion of the ablation applicator) and the further temperature sensor is preferably arranged towards a distal end of the lumen (i.e. in a distal portion of the ablation applicator). Thereby, a temperature difference between the proximal and the distal end may be detected and compensated for.

In an embodiment, the ablation applicator may further comprise a shaping structure, such as a super-elastic shape memory structure, arranged within the inner lumen and adapted to provide the tubular body with a desired shape. The shaping structure preferably comprises nitinol. Further, the shaping structure preferably comprises an austenite finish temperature (Af-temperature) below 12° C., such as below 6° C. Thereby, the super- or pseudo-elastic properties can be obtained at body temperature (i.e. around 37° C.), such that the shaping structure can maintain the desired shape of the tubular body during and after insertion of the ablation applicator into a patient.

In an embodiment, the ablation device may further comprise a positioning catheter adapted to be positionable in a heart (wherein the ablation catheter and the positioning catheter may be different members being however functionally coupled to one another). However, in other embodiments, the provision of an ablation catheter alone is sufficient and a separate positioning catheter may be omitted, for instance if a mechanism is provided which triggers the ablation applicator to be converted between different shapes, for example from an insertion shape (for instance elongate) to an ablation shape (for instance helical or curved), or vice versa. Optionally, the positioning catheter may comprise a fixation mechanism (such as a balloon or a fixation helix) for fixing the positioning catheter in the heart.

The aspects defined above and further aspects of the invention are apparent from the examples of embodiment to be described hereinafter and are explained with reference to these examples of embodiment.

FIG. 3 shows an ablation applicator inserted for treating hypertension by neural modulation in a kidney according to an exemplary embodiment of the invention.

FIG. 4 shows the anatomical conditions of kidneys in which the cryoapplicator of FIG. 3 can be implemented.

FIG. 5 shows a tubular body of an ablation applicator according to an exemplary embodiment of the invention.

FIG. 6 to FIG. 8 show examples illustrating constitution of a voxel of the tubular body of FIG. 5 according to different exemplary embodiments of the invention, wherein in each case a polymeric matrix material is filled with particles of a polymeric or non-polymeric filling material.

FIG. 11 shows a cross-section of an ablation applicator according to another exemplary embodiment using a combination of different kinds of fibers.

FIG. 12 shows an ablation applicator according to another exemplary embodiment having another combination of different kinds of fiber.

FIG. 13 is a diagram showing the angular dependency of the cooling power flow of the ablation applicators of FIG. 11 and FIG. 12.

FIG. 14 shows a cross section of an ablation applicator for an ablation device according to an exemplary embodiment of the invention, wherein a circumferential variation of particles embedded in the matrix ensures a circumferentially varying thermal conductivity of the ablation applicator.

Figure 22:
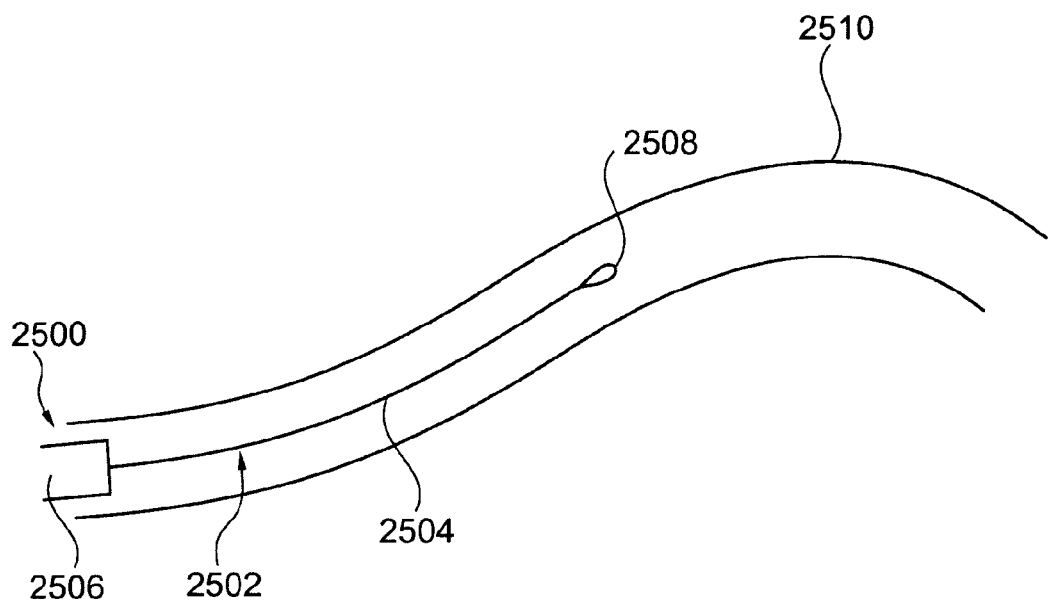
Figure 23:
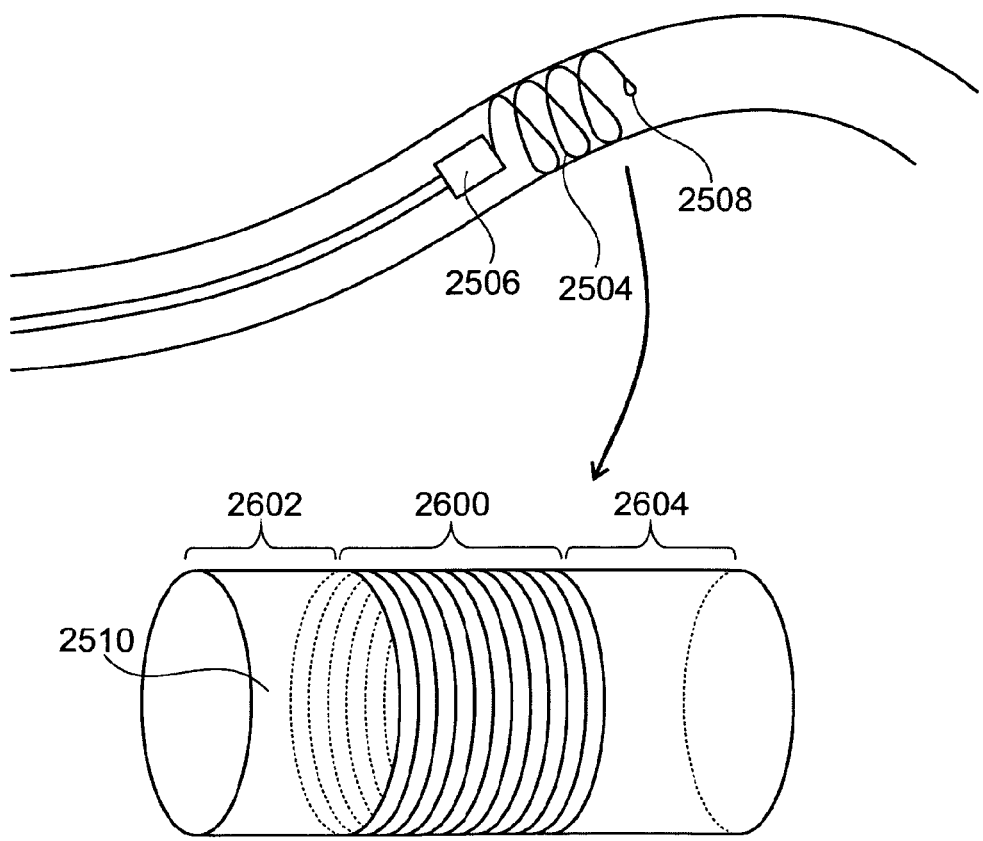

FIG. 22 and FIG. 23 schematically illustrate an ablation device according to another exemplary embodiment of the invention in which an ablation applicator can be converted from an elongated state to a helical configuration, so that in the latter configuration ablation in a artery of a kidney is possible along a basically cylindrical ablation area.

The illustration in the drawing is schematically. In different drawings, similar or identical elements are provided with the same reference signs.

In an embodiment, a cryoapplicator with fiber-reinforced plastic is provided. Particularly, one embodiment provides a cryoapplicator tubing made from a combination of filled and unfilled polymer. At least in one quarter of the circumference the heat transfer parameter may be larger than 1500 W/m²K, and at least in one quarter of the circumference it may be smaller than 1200 W/m²K.

For the construction of cryo-applicators it may be desirable to adjust different material properties in a broad spectrum of physical parameters. For example heat conduction should be high in a portion having contact with the target tissue while in a portion opposed to the blood stream heat it should be low for avoiding undesired waste of cooling medium. Also mechanical properties may be tailored to a specific application. For example bending stiffness of an applicator should be kept low enough for moving it with ease through a curved tube (geometry of a vessel or an introducer) but high enough to span up a flexible target tissue structure (for example the atrial muscle) for ensuring sufficient mechanical contact between the applicator and the tissue. Similarly torsional stiffness can be selected above a specific value to ensure that the applicator can be rotated but additionally it may be requested that it remains also below a specific value to ensure that a desired deformation can be performed. This deformation may be needed when the applicator has to take a specific shape for the application of cryoablation. Here the material properties can be selected such that kinking is avoided. Furthermore, for increasing the functional safety of a cryoablation device, the applicator shall be pressure resistant withstanding a high burst pressure but also a vacuum condition. In certain embodiments it is possible that the material properties vary over the length of an applicator.

When metallic structures are provided for cryoapplicators they may be simultaneously used as recording electrodes for electric signals. Here a large surface may be needed for sufficient heat exchange with the tissue during cryoablation. On the other hand for a better local resolution of an electrocardiogram (ECG) recording a smaller electrically conduction may be desirable. Thus, at least a portion of the applicator shall be a thermal conductor but an electrical isolator.

Figure 1:
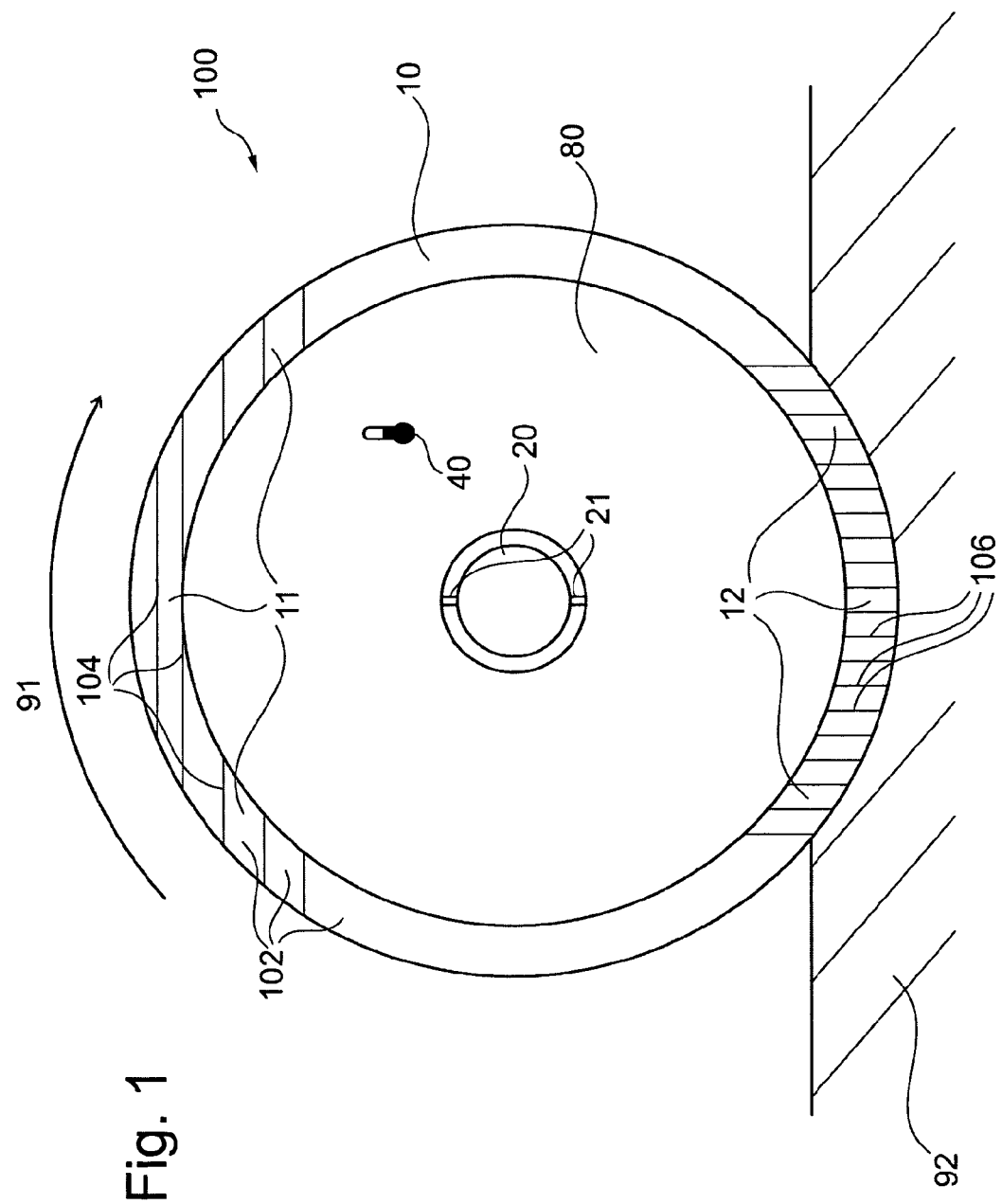
FIG. 1 is the cross-section of a cryoapplicator of a cryogenic ablation device with a circumferentially varying thermal conductivity according to an exemplary embodiment of the invention.

FIG. 1 shows a cross-section of an ablation applicator 100 for a cryogenic ablation device according to an exemplary embodiment of the invention.

The ablation applicator 100 has a tubular body 10 which may also be denoted as an outer tubing jacket and which defines a lumen functioning as a boiling chamber 80 of refrigerant supplied as an ablation medium to the ablation applicator 100. More precisely, a liquid refrigerant is supplied to an interior of a tubular ablation medium supply line 20 in a liquid form. Upon traversing a number of recesses 21 in the tubular ablation medium supply line 20, the ablation medium expands in the boiling chamber 80. Due to this expansion, a temperature reduction occurs which cools an inner surface of the tubular body 10 of the ablation applicator 100.

The tubular body 10 comprises a hollow cylindrical polymer matrix 102 in which a plurality of particles are embedded sectionwise. More precisely, in an isolating zone 11 of the tubing 10, thermally isolating particles 104, for instance in form of thermally isolating fibers or in form of thermally isolating beads, are embedded.

In contrast to this, a thermally conducting zone 12 in another circumferential portion of the tubing 10 has embedded therein second thermally conductive particles 106, for instance in the form of thermally conductive fibers or in form of thermally conductive beads.

As can be taken from the schematic drawing of FIG. 1, both the first thermally isolating particles 104 and the second thermally conductive particles 106 are embedded in the matrix 102. In other words, the matrix material 102 of polymer forms a base material in which the individual particles 104, 106 are embedded. Therefore, the thermal properties around the circumference of the tubing 10 are adjusted sectionwise by a combination of the selection of the materials of the matrix 102 and the particles 104, 106, their density distribution along the circumference of the tubing 10, and their sectionwise orientation.

Hence, a principal cross section of the cryoapplicator tubing 10 designed for the creation of elongated lesions is shown in FIG. 1. The outer jacked tubing 10 of the cryoapplicator has a kind of cylindrical shape defined by an elongated structure which is in contact with the tissue 92 essentially along a line. The cross section of the applicator (FIG. 1) has a circular or oval shape. The refrigerant supply line 20 contains the micro-holes or recesses 21 for delivering refrigerant along the active section of the cryo-applicator tubing. One or more temperature sensors 40 (for example thermocouples, PTC or NTC-sensors) may be used for monitoring the temperature along the tubing 10. The remaining cross section forms the boiling chamber 80 which defines also the refrigerant return path. The refrigerant might be removed actively (low pressure evacuation) for preventing refrigerant exit in the case of leakage of the outer sealing of tubing 10.

For the creation of elongated lesions, multiple temperature sensors 40 may be used for monitoring ablation along a line having a length of several cm. In particular, at least one sensor in the distal portion of the cryo-applicator and one in its proximal portion may be used.

One part of the cross section is in tissue contact. Thus, a high thermal conductivity is desired in a part of the cross-section termed the conducting zone 12. This zone is indicated by a vertical hatching symbolizing an increased heat transfer from the boiling chamber 80 within the cryoapplicator to the tissue 92. Measures for increasing the heat transfer involve use of material of high thermal conductivity and/or narrow wall thickness and will be described in detail below. Opposite to the conduction zone an undesired heat exchange with the blood stream 91 takes place. Here the isolating zone 11 reduces the heat transfer. This is indicated by a horizontal hatching symbolizing blocking of the heat transfer. Measures for reducing the heat transfer involve use of material of low thermal conductivity, larger wall thickness and will be described in detail below.

The ratio a of thermal conductivity $\lambda_c$ across the cross section (essentially in radial direction in FIG. 1) and the wall thickness d yields an quantitative estimate of the heat transfer property ($a=\lambda_c/d$). The conductive zone 12 is defined such that the value a is larger than 1500 W/m²K and more particularly larger than 2000 W/m²K. In the isolating zone 11 the value a is smaller than 1200 W/m²K and more particularly smaller than 1100 W/m²K.

Note that the isolating zone 11 in FIG. 1 forms a considerable portion of the circumference of the cross-section (more than one quarter but less than three quarters and more particularly more than one third but less than two thirds).

Figure 2:
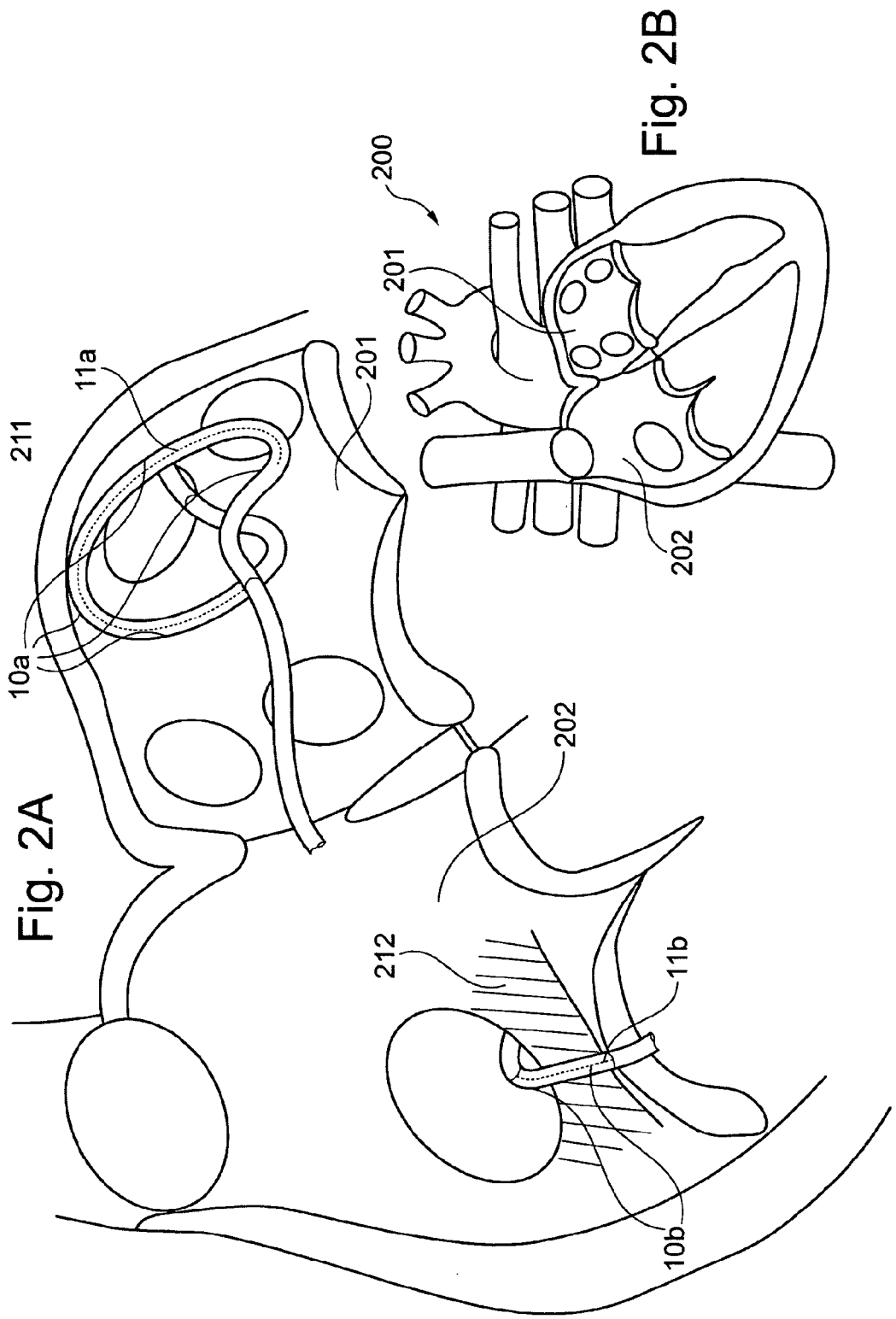
FIG. 2A shows a cryoapplicator in a loop-like structure for ablating tissue around a pulmonary vein ostium in the left atrium of the heart according to an exemplary embodiment of the invention.
FIG. 2B shows the anatomical conditions in a heart in which the cryoapplicator of FIG. 2A can be implemented.

In FIG. 2A and FIG. 2B some example embodiments illustrate how the cross section of FIG. 1 might be orientated in order to create elongated lesions in cardiac tissue.

In FIG. 2A a cryo-applicator tubing 10a forms a loop like structure for ablating tissue around a pulmonary vein ostium 211 in the left atrium 201 of the heart 200 for treating atrial fibrillation. A dashed line marks the orientation of the isolating area 11a away from the tissue.

In FIG. 2A a cryo-applicator tubing 10b is shaped along the cavotricuspid isthmus 212 in the right atrium 202 for treating atrial flutter. Again a dashed line marks the orientation of the isolated area 11b away from the tissue.

If the creation of a continuous lesion in cardiac tissue is desired the spacing of the refrigerant exit holes or recesses 21 within the tubing 10 (see for instance FIG. 14) may be smaller than 8 mm and more particularly smaller than 6 mm. For ensuring that a uniform distribution of the refrigerant exits along the cryo-applicator, the diameter or cross-sectional area of the recesses may vary. The cross-sectional area may be smaller for proximal recesses and larger for distal recesses in order to compensate for potential pressure variations along the refrigerant supply line. Variations in cross-section can be achieved by adjusting the diameter of an essentially circular recess or the shape of the recesses from circular to oval or elongated. The cross-sectional area may vary continuously from one recess to the next. However, also step like variations are possible with a group of neighboring recesses of essentially same area and a step like variation of the area to the next group of recesses. The total increase in area from the smallest area to the largest may be between 5% and 40% and more particularly between 10% and 25%. Typically, the diameter of the circular recesses is between 10 μm and 100 μm.

At its distal end, the refrigerant supply line might be closed. Alternatively the cross section of the distal end can be reduced by inserting a short piece of tubing with a narrow distal diameter. Typically, this diameter is not larger than 100 μm.

It may be advantageous to place the temperature sensors (e.g. thermocouples 40 in FIG. 1) next to the recesses. In this situation, they can measure the refrigerant temperature right in the area of highest heat transfer to the body. This temperature will closely correlate with the boiling chamber pressure.

In FIG. 3 and FIG. 4 exemplary embodiments illustrate how the tubing 10 in FIG. 1 might be applied for treating hypertension by neural modulation. Schematically the left and right kidney 301 and 302 are depicted in FIG. 4. The left and right renal arteries 311 and 312 are carrying the blood flow from the aorta 306 to the kidneys 301, 302. In the adventitia surrounding the smooth muscle fibers of the renal arteries 311 and 312 the renal innervations are located which contribute to blood pressure control. Partial or complete ablation of these innervations can be applied for reducing blood pressure.

In FIG. 3 a helically shaped cryo-applicator 10c is inserted into the real artery for neuromodulation in treatment of hypertension. A thermally conducting zone 12c is located essentially in an outside orientation on the helical tubing such that it is in contact with the vessel wall. In two locations this is indicated exemplarily. The isolating zone is located essentially in an inside orientation of the helix such that it is directed towards the blood stream. For the shown embodiment the cryo-applicator 10c is mounted on a positioning catheter 410. This positioning catheter 410 can slide within a lumen of a catheter shaft 401 which is rigidly connected with the cryo-applicator 10c. A sheath or introducer (steerable or fixed curve) may be used for assessing the renal arteries 311. Pulling back the shaft 401 relative to the positioning catheter 410 stretches the catheter to an essentially elongated shape which allows the insertion into the body. Advancing the shaft 401 in a forward direction relative to the positioning catheter 410 triggers the formation of helical shape of the cryo-applicator 10c. The formation of this shape may be supported by a component made from a shape-memory alloy (such as component 50 in FIG. 14). For the placement of the supporting positioning catheter 410 a guide wire 408 may be used. The lumen which contains the guide wire 408 may be also used for the admission of a contrast agent which supports the visualization of the renal artery 311 in an imaging modality such as for example X-ray (particularly computed tomography, CT), MRI (magnetic resonance imaging) or ultrasonic. Alternatively or additionally a tip 402 of the positioning catheter 410 may be shaped such that it can be inserted in a branching of the vessel for increasing the stability of the positioning catheter 410. If the positioning catheter 410 should take up also pulling forces an inflatable balloon 403 may be foreseen. A sleeve 405 may provide the connection of the cryo-applicator 10c with the positioning catheter 410. In yet another embodiment a balloon 403 may be omitted and the sleeve may be integrated into the tip 402.

If the creation of a continuous helical lesion in the vessel wall is desired the spacing of the refrigerant exit holes 21 within the tubing (FIG. 14) will be smaller than 8 mm and more particularly smaller than 6 mm. If the creation of discrete point like lesions is desired in a heart the spacing will be larger than 8 mm and more particularly larger than 10 mm. In yet another embodiment the balloon 403 may be arranged proximally from the applicator. In this arrangement inflating the balloon will block the blood flow along the renal artery and, thus, decrease the thermal load during freezing.

In yet another embodiment the positioning catheter 410 is omitted. Thus by pulling back the guide wire 408 the shape memory component 50 in FIG. 14 will force the applicator 10c to take its helical shape. This embodiment may contribute to reducing the inner diameter of the sheath 411 which may be of advantage for narrow vessels. Furthermore, no mechanism is needed for moving the positioning catheter and shaft relative to each other which may contribute to a simpler and cheaper catheter design.

In yet another embodiment the guide wire 408 is omitted. The positioning catheter 410 (which may be steerable or may be not steerable but controlled by the sheath 411) is used to access the vessel. The cryo-applicator is brought from its passive stretched configuration to its active helical configuration by moving positioning catheter and applicator relative to each other.

In yet another embodiment both positioning catheter 410 and guide wire 408 are omitted. The transition from passive to active configuration is solely triggered by an shape-memory component 50 when moving the cryo-applicator 10c out of the sheath 411. This can be accomplished by pulling back the sheath or by advancing the cryo-applicator 10c.

In yet another embodiment the active configuration of the cryo-applicator 10c is not a helix but an arc-like geometry which ensures sufficient wall contact with the vessel.

FIG. 5 shows again a tubular body 10 together with a volume element or voxel V. Detailed illustrations of the constitution of the volume V in three different embodiments are shown in FIG. 6 to FIG. 8.

According to FIG. 6, elongate fibers 13 having a high aspect ratio are aligned in a matrix 19 parallel to one another and parallel to a symmetry axis 500 of the tubing 10.

In the embodiment of FIG. 7, fibers 14 are aligned isotropically, i.e. without any orientation along a preferred direction, thereby resulting in isotropic heat transfer properties.

In FIG. 8 the volume V comprises again material of the matrix 19 in which bead-like particles 15 with an oval cross section are embedded.

Hence, in FIG. 5 to FIG. 8 example embodiments of filled polymers in the context of the present invention are described. FIG. 5 shows a piece of a cryoapplicator tubing 10 with a volume V which may be composed of polymeric matrix material filled with a polymeric or non-polymeric filling material. The filling material may be arranged in long, orientated fibers 13 (FIG. 6), in short not-orientated fibers 14 (FIG. 7) or in small particles 15 (FIG. 8). Here, fibers are essentially cylindrical structures with narrow cross sections (below 50 µm maximal diameter and more specifically below 25 µm maximal diameter) which can be long (more than a few millimeters of length) or short (less than a few millimeters of length). Long fibers 13 (FIG. 6) may be arranged by production techniques in a controllable fashion (for example pultrusion of fibers 13 and matrix material 19) such that they may be arranged essentially in parallel to the axis 500 of cryo-applicator tubing 10 or may be wound around the circumference of an applicator tubing in a defined angle. Here, from a macroscopic point of view anisotropic material properties along and across to fiber orientation may be defined. The term macroscopic may be understood such that cubic volume V contains a plurality of filling elements 13, 14 or 15 such that average material properties can be defined over the spatial extension of volume V. Exemplarily an anisotropic macroscopic material property (which can be for example thermal conductivity) is indicated by arrows $m_x$, $m_y$, $m_z$. In contrast, short fibers may be introduced within the material without control of orientation (for example extrusion of a polymeric granulate with short fibers) resulting in a pattern of randomly orientated or non-orientated fibers 14. In this case macroscopic material properties are essentially isotropic ($m_x \approx m_y \approx m_z$). Similar the filling material might be composed of particles such as beads 15 (see FIG. 8, filling elements of essentially oval shape with a maximal spatial extent below 50 µm and more specifically below 25 µm). Here, again orientation of the filling material is not controlled during production and the macroscopic material properties are essentially isotropic ($m_x \approx m_y \approx m_z$).

The relative filling volume is the ratio of the volume within tubing 10 occupied by the filling material 13, 14 or 15 and the entire volume of the tubing 10. The relative filling volume may be a value below 80%.

The matrix material 19 used for embodiments described in FIG. 6 to FIG. 8 is a polymeric material which should provide a dense and leakage proof connection between the particles or filling elements (fibers 13, 14 or beads 15). The polymer shall ensure a continuous connection between filling elements such that macroscopic material properties $m_x$, $m_y$, $m_z$ obtained are a weighted mean of matrix and filling element property. For example when pulling a tubing 10 along its major axis stretching of the material may be governed by a macroscopic (weighted average) elastic modulus which is defined by the material properties of matrix and filling material, the relative filling volume and fiber orientation in case of orientated fibers. Thus, the matrix material provides an essentially force fit connection from fiber to fiber ensuring that a mechanical load is distributed over the matrix and the filling material. Similarly, if a temperature gradient is applied across a macroscopic portion of a filled tubing (i.e. a portion several times larger than the maximum fiber diameter or maximal particle size) heat flow will be governed by a macroscopic (weighted average) thermal conductivity which is defined by the material properties of matrix and filling material and the relative filling volume. Additionally in the case of orientated fibers macroscopic conductivity will be a tensor with a different value along and across fiber orientation. Examples of matrix materials for the embodiments described above are polyurethane, silicone or polyamide. However, also other polymeric matrix materials may be used. Generally, the use of an electrically non conductive matrix material will result in a high resistive compound material. If a conductive filling material is used the compound material may conduct high frequency alternating due to capacity effects. Electrically conducting polymers with an electrically conducting filling material may be used for designing compound materials with a desired electrical resistance in the direct current range.

Referring back to FIG. 6, orientated fibers 13 may be foreseen for alternating thermal and mechanical material parameters in an anisotropic fashion. For example, carbon or metallic fibers (for example silver) may be used to increase the thermal conductivity of the material (along and to a smaller degree across fiber orientation) simultaneously with mechanical robustness (particularly tensile strength in fiber direction). For increasing mechanical robustness without or with a relatively small increase of thermal conductivity fiber materials such as nylon, glass or Teflon (polytetrafluoroethylene, PTFE) might be used. Glass fibers will result in a relatively stiff compound material along fiber direction while nylon fibers may allow the design of a more flexible compound material.

Adjustable essentially isotropic material properties may be obtained by the embodiments described in FIG. 7 and FIG. 8. For example short not orientated carbon fibers in a polymer matrix may be applied for designing a mechanically relatively stiff compound material, with a high thermal conductivity but low electrical conductivity. Metallic particles (for example Tungsten or silver) in a polymeric matrix may also result in a high thermal conductivity at a low electrical conductivity but will result in a mechanical softer material.

Note that the interface between the matrix and filling material can severely affect the macroscopically observed material properties. If the matrix material does not or purely coat the filling material, tiny gaps in the compound material may occur. This might be used to decrease thermal conductivities.

For a high thermal conductivity, a good coating of the filling material by the matrix material is essential. This can be achieved by surface treatment of the filling material or by proper selection of the matrix material. For example, the polyurethane with the brand name Textin displays a good coating with tungsten. In contrast, polyurethane with the brand name Pellethane poorly coats tungsten.

Thus, by properly selecting matrix and filling material physical parameters of the compound material can be adjusted in a wide range. Thermal, mechanical and electric macroscopic parameters may be tailored separately. Furthermore, macroscopic material properties may be chosen in an isotropic or anisotropic way.

In Table 1 some values are listed which enable the computation of the heat transfer coefficient (above denoted as "a") for some examples of fiber reinforced polymers. These values are obtained from a finite element model of composite material. This model considers the idealized situation that no polluting inclusions (air bubbles, surface coating, etc.) are present in the matrix. Thus, they are an estimate of a the highest obtainable conductivities.

TABLE 1

Conductivity values composite materials

| material matrix | conductivity matrix [W/mK] | material fibre | conductivity fibre [W/mK] | volume % fibre | conductivity along fibre [W/mK] | conductivity across fibre [W/mK] |
|---|---|---|---|---|---|---|
| silicone | 0.16 | carbon | 17 | 40% | 6.90 | 0.41 |
| silicone | 0.16 | carbon | 17 | 45% | 7.74 | 0.47 |
| silicone | 0.16 | carbon | 17 | 50% | 8.58 | 0.55 |
| silicone | 0.16 | carbon | 17 | 55% | 9.42 | 0.65 |
| silicone | 0.16 | carbon | 17 | 65% | 10.26 | 0.77 |
| silicone | 0.16 | carbon | 17 | 70% | 11.11 | 0.94 |
| silicone | 0.16 | quartz | 1.38 | 40% | 0.65 | 0.31 |
| silicone | 0.16 | quartz | 1.38 | 45% | 0.71 | 0.34 |
| silicone | 0.16 | quartz | 1.38 | 50% | 0.77 | 0.38 |
| silicone | 0.16 | quartz | 1.38 | 55% | 0.83 | 0.42 |
| silicone | 0.16 | quartz | 1.38 | 65% | 0.89 | 0.46 |
| silicone | 0.16 | quartz | 1.38 | 70% | 0.95 | 0.51 |
| silicone | 0.16 | nylon | 0.2 | 50% | 0.18 | 0.17 |
| PUR | 0.18 | nylon | 0.2 | 60% | 0.19 | 0.19 |

Using silicone as a matrix material with orientated carbon fibers at a fiber volume ratio of 60% a conductivity of 10.7 W/mK is obtained along the fibers and $\lambda_c=0.65$ W/mK across the fibers. As fiber orientation is parallel to the tubing $\lambda_c$ must be applied for the computation of the heat transfer coefficient. For a wall thickness of d=0.18 mm a value $a_{FRP}=3610$ W/m$^2$K is obtained for the conducting area which is above the desired values listed above. Adding an isolating layer made from the matrix material silicone (thermal conductivity 0.16 W/mK) of 0.11 mm thickness a heat transfer coefficient of $a_{Matrix}=1450$ W/m$^2$K is obtained for the isolating layer. However, in the isolating region the fiber reinforced tubing and the isolating layer are thermally in series and the total heat transfer parameter of the isolating layer is $a_{iso}=1/(1/a_{matrix}+1/a_{FRP})=1035$ W/m$^2$K. This value is below the desired values listed above.

Figure 9:
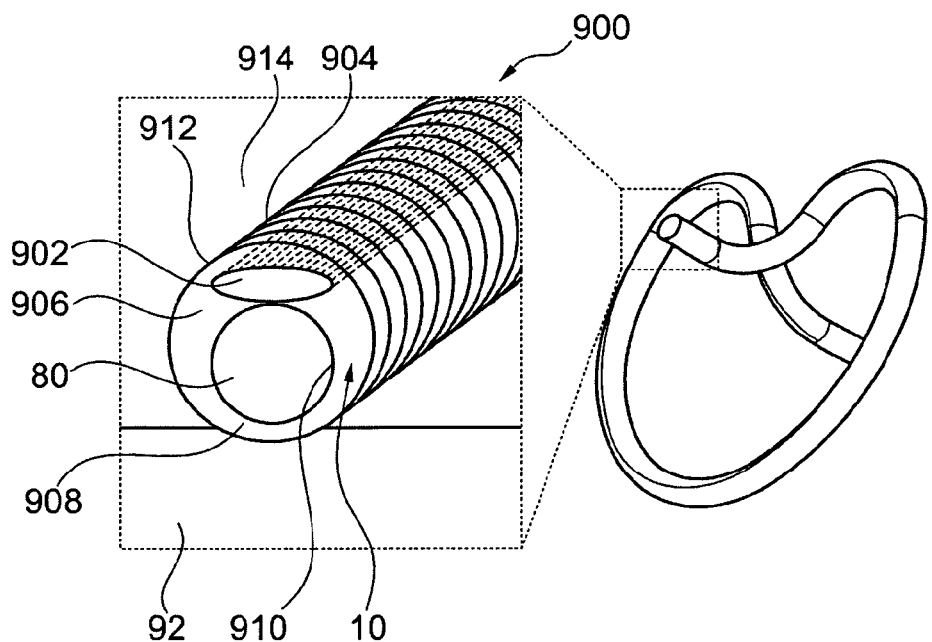
FIG. 9 shows a three-dimensional image of a portion of a loop-like ablation applicator in which various measures are taken for circumferentially varying the thermal conductivity by a combination of matrix material and a spatially varying distribution of different kinds of fibers.

In FIG. 9, an ablation applicator 900 according to another exemplary embodiment of the invention is described. FIG. 9 shows a three-dimensional view of a cross-section of such an ablation applicator 900 as well as an overview of the entire ablation applicator 900 being configured similar as in FIG. 2A. Again, for ablation, it is necessary to transfer cooling power from boiling chamber 80 to surrounding tissue 92. It is further noted that, as indicated with reference number 914, an upper portion of the tubing 10 is surrounded by blood. It is mentioned that the interior of the boiling chamber 80 is not shown in detail in FIG. 9 and can be configured for instance in a way as it is shown in FIG. 1. The tubular body 10 comprises also in this embodiment a matrix of polymer material and a plurality of particles accommodated therein. First particles are fibers 902 which extend along a longitudinal access of the tubular body 10. They are also called 0° fibers. Furthermore, so-called 90°-fibers are provided as second particles in the form of fibers 904 circumferentially wound in a helical way around an outer cylindrical surface of the tubular body 10. As a result of this arrangement, a thermally isolating zone 906 is formed in a region where the 0° fibers 902 extend. Additionally, the wall thickness of the tubular body 10 is here larger compared to other sections which further renders heat transfer inefficient in this region. On the other hand, in a cooling zone 908, the thickness of the tubular body 10 is small so that a proper heat transfer is possible in this section. It can also be taken from FIG. 9 that the surface 910 delimiting the inner lumen on the one hand and the outer surface of the tubular body 10 on the other hand shown in reference number 912 are eccentric. This also contributes to the anisotropic thermal conductivity properties of the ablation applicator 900. A structure as occupied by the fibers 902 can be manufactured by pultrusion, filament winding, pullwinding, braiding, or extrusion, for instance.

Figure 10:
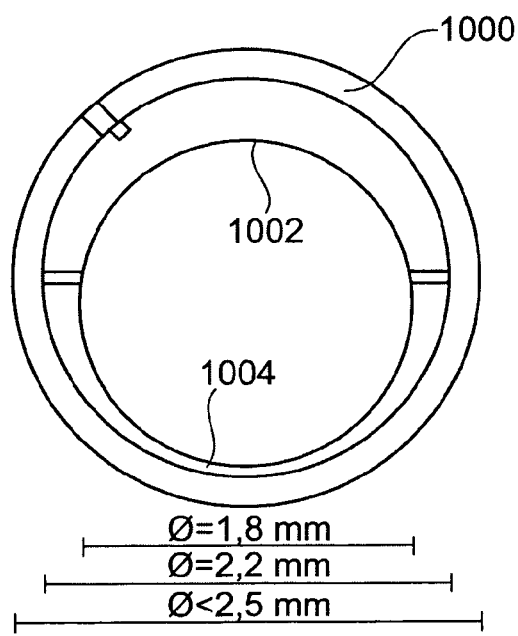
FIG. 10 shows a cross-section of an ablation applicator according to an exemplary embodiment of the invention with a circumferentially varying thermal conductivity obtained by a combination of a spatially varying matrix material and particles accommodated therein and thereon.

FIG. 10 shows a cross-sectional view of an ablation applicator according to an embodiment of the invention in which different zones of fibers can be distinguished. Carbon fibers 1000 are circumferentially or helically wound around a core which consists of an upper half circle of nylon fibers 1002 and a lower half of carbon fibers 1004. The orientation of the fibers shown in FIG. 10 is longitudinal, i.e. perpendicular to the paper plane of FIG. 10. The thickness of the wall of the ablation applicator of FIG. 10 is circumferentially varying which also contributes to the circumferential variation of the thermal conductivity.

FIG. 11 shows another cross-section of an ablation applicator 1100 according to an exemplary embodiment of the invention. In this case, quartz fibers 1102 are provided along an inner portion of the ablation applicator 1100 with a spatially dependent thickness. A tubing from carbon fibers 1104 is provided to form an outer circumference of the ablation applicator 1100 and has a thickness which is homogeneous.

FIG. 12 shows an ablation applicator 1100 according to another exemplary embodiment in which the carbon fibers 1104 form the inner portion of the tubing 1200, whereas the quartz fibers 1102 with the circumferentially varying thickness are provided to form the outer circumference of the tubing 1200.

In the embodiments of FIG. 11 and FIG. 12, the quartz fibers 1102 provide an insulating layer, whereas the carbon fibers 1104 provide a thermally conductive layer.

FIG. 13 shows a diagram 1300 having an abscissa 1302 along which a circumferential angle is plotted. Along an ordinate 1304 a power density of transferred cooling power per area is plotted. A first curve 1306 relates to a scenario in which no isolation layer 1102 is foreseen at all. A second curve 1308 relates to the scenario of FIG. 11 with an inner isolation layer 1102. A third curve 1310 relates to the scenario of FIG. 12 with the isolation layer 1102 at the outer circumference of tubing 1200.

The assessment of the heat transfer parameter yields only an estimation of the heat transfer across a wall as it does not consider the spatial arrangement of the layers. For example, FIG. 11 to FIG. 13 compare the heat flow of two embodiments computed by a finite element simulation. In FIG. 11 the isolating layer 1102 is inside the tubing, while in FIG. 12 the isolating layer 1102 is outside. It is assumed that in the tubing carbon fibers 1104 are included which are orientated in an essentially azimuthal direction (winding of fibers around the longitudinal winding of the tubing). As can be seen from the heat flux density (FIG. 13) on the outer circumference (computed by finite element analysis), arranging the isolating layer 1102 outside results in a more effective separation of thermally conducting and isolating zone as this design avoids heat transfer around the isolating zone guided along the fibers in the polymeric structure.

In some embodiments, a thin coating may be applied on the outer surface of the applicator for ensuring biocompatibility. Also, in some embodiments a leak-proof layer may be applied to the inner surface for avoiding that refrigerant enters the potential tiny gaps between the fibers and the matrix material. Also such layers contribute to the heat transfer parameter as a structure which is thermally in series with other layers.

FIG. 14 shows an application applicator 1400 according to another exemplary embodiment of the invention which is similar to the embodiment of FIG. 1. However, in contrast to the embodiment of FIG. 1, thermally isolating particles 104 are omitted. The matrix is formed of polyurethane in the shown embodiment. Furthermore, tungsten particles 106 are embedded in a lower section in order to provide for a strong thermal coupling to the tissue 92.

In the shown embodiment, it may be desirable to avoid the use of spatially well orientated fibrous structures but to add a filling material of small pieces of not orientated fibers or even particles to adjust the material parameters such that essentially isotropic macroscopic properties are obtained. For increasing thermal conductivity for example short not orientated carbon or glass fibers or particles or metallic particles (tungsten) may be added to the polymer matrix material, as illustrated by reference numeral 106 in FIG. 14. Such structures can be produced by standard methods such as extrusion. In one embodiment, small tungsten particles are added such that the tubing material contains 40 mass percent of tungsten. In addition to altering thermal conductivity, the filling material may simultaneously change other physical properties, such as X-ray (particularly computed tomography, CT), MRI (magnetic resonance imaging) or ultrasonic contrast in a desired fashion. Thus the user is able to verify if the conduction side is attached to the tissue by X-ray inspection. If for example the polymer matrix is polyurethane with a thermal conductivity of about 0.2 W/mK, adding up to 60 mass percent tungsten will increase thermal conductivity to about 0.3 W/mK. In other words, only the half of the tubing which is in contact with tissue contains the tungsten particles. This material modification in combination with a modest reduction of wall thickness increases the heat transfer parameter to a value larger than 1500 W/m$^2$K in one section of the ablation applicator. In the remaining half, no tungsten is included and a modest increase of wall thickness is foreseen to decrease the heat transfer parameter to a value smaller than 1200 W/m$^2$K in another section. The different appearance of these two sides in X-ray or computed tomography may help an operator to position the ablation device.

In FIG. 14, a corresponding exemplary embodiment is shown where the realization of a thermally conducting region 12 (in contact with the tissue 92) and isolating region 11 is obtained by varying wall thickness together with the filling material. In the conducting region 12, for a wall thickness of 0.16 mm and polyurethane (PUR) with 60% tungsten filling a heat transfer parameter $a_c$=1875 W/m$^2$K is obtained. In the isolating region 11 without filling and a wall thickness of 0.2 mm a heat transfer parameter $a_i$=1000 W/m$^2$K is obtained.

A support structure 30 like a helical coil or a wire-framework may be inserted to protect the tubing from kinking. A superelastic shape memory structure 50 may be inserted for giving the cryo-applicator a desired shape.

Nitinol may be used for obtaining super- or pseudo-elastic material properties at body temperature. When using nitinol in combination with cryo-application, it may be of advantage if the phase change of metallic structure from the elastic austenite phase to the martensite phase occurs at low temperatures. In particular, the active austenite finish temperature of the material might be adjusted below 12° C. and more particularly below 6° C. Chrome doted nitinol might be used in combination with proper heat treatment for obtaining the desired low Af-temperatures.

For ensuring mechanical stability of the desired shape, the superelastic material should be selected such that its loading and unloading plateau in the stress-curve is high. In particular, the loading plateau should be above 450 MPa at body temperature, and the unloading plateau should be above 180 MPa (again at body temperature).

In another embodiment the refrigerant supply is made from a superelastic tube (for example nitinol tube with an active Af temperature well below body temperature) combining the function of components 20 and 50 in one component. In yet another embodiment, the wire-frame 30 is made from a shape-set superelastic material combining two functions in one embodiment.

Figure 15:
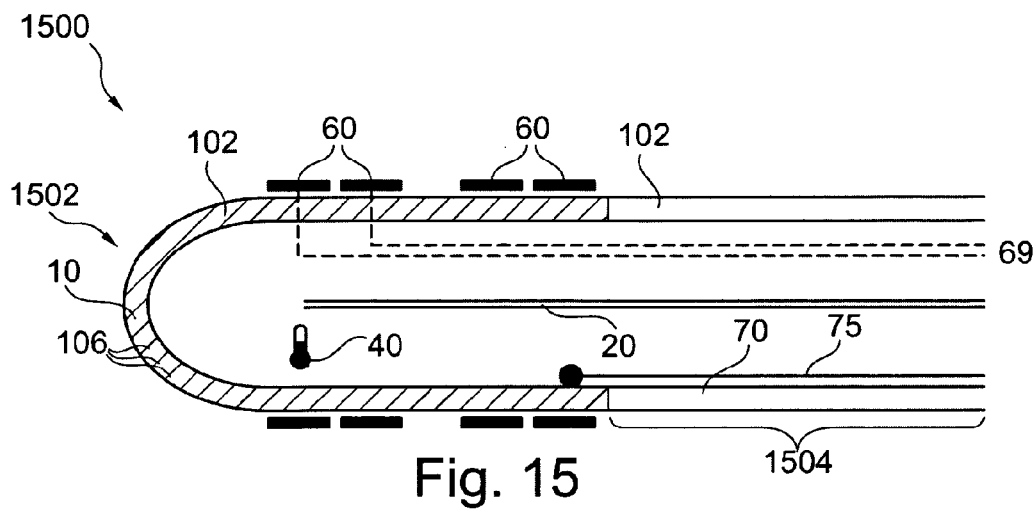
FIG. 15 to FIG. 17 show ablation applicators of ablation devices according to exemplary embodiments of the invention in which selectively a tip at a closed end of a tubular body is rendered highly thermally conductive by embedding particles in a polymer matrix, wherein a remainder of the tubular body is thermally insulating in view of the absence of particles in these remaining sections.
Figure 16:
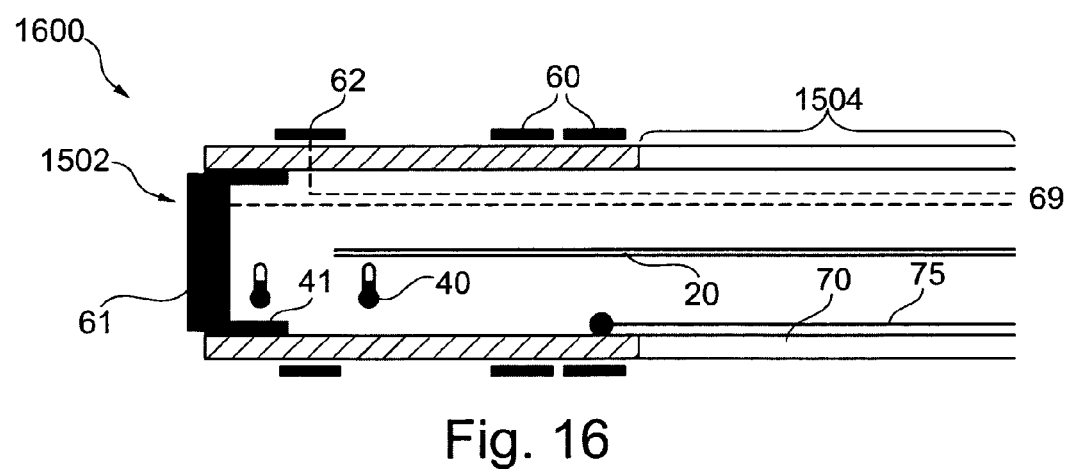
Figure 17:
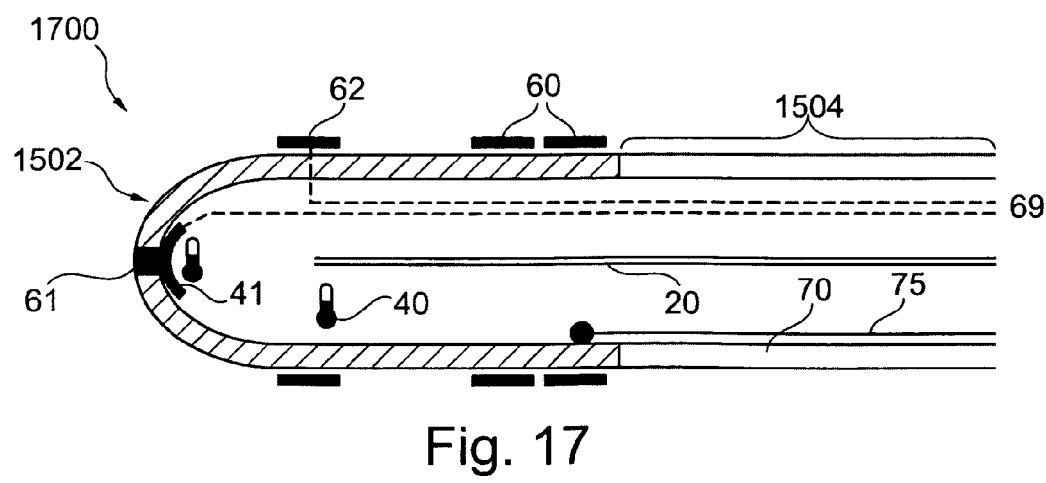

FIG. 15, FIG. 16 and FIG. 17 show ablation applicators 1500, 1600 and 1700, respectively, according to exemplary embodiments of the invention. All these three embodiments have in common that the tubular body in this case has a cupola-shaped closed end 1502 forming a rounded tip of the tubular body. As can be taken from FIG. 15 to FIG. 17, only the closed end 1502 includes filling particles in the form of thermally conductive particles 106 embedded in the matrix material 102. Thus, only the end section 1502 of the ablation application 1500, 1600 and 1700 is thermally conductive, whereas a rear portion 1504 is thermally insulating. In other words, in the rear portion 1504 the tubular body only consists of matrix material which has a poor thermally conductivity in the present embodiment.

It should be said as well that in the embodiments of FIG. 16 and FIG. 17, front portions of the tip 1502 are partially formed by metallic material, see reference numerals 61, 41.

In view of its proper thermal connectivity, also this metallic material may contribute to the thermal conduction. Therefore, in each of the embodiments of FIGS. 15 to 17 a cool tip is provided, i.e. a closed end 1502 with locally increased thermal conductivity. Therefore, ablation of a tip like section of tissue (not shown in FIG. 15 to FIG. 17) is possible with these embodiments.

In some applications the treatment of small, essentially focal tissue structures might be of interest. For example for the ablation of cardiac arrhythmia the elimination of conduction across a Kent bundle (Wolff-Parkinson-White syndrome) may be the target. The spatial extension of a Kent bundle is in the order of up to a few millimeters. During ablation therapy its location within the heart may be identified by analyzing the intracardiac electrogram waveform recorded on the tip of the ablation catheter (fusion of atrial and ventricular signal marks the Kent bundle). Cryoablation catheters may have a metallic tip of 5 mm to 10 mm length for providing sufficient contact surface for heat exchange with the tissue. Here the metallic tip may act simultaneously as a recording electrode and boiling chamber for the refrigerant. However, for recording local electric activity the spatial extension of the electrode should be small while for successful cryotherapy a relatively large spatial extension is needed. Here fiber reinforced polymers or polymers filled with thermally conductive compounds may be used according to exemplary embodiments of the invention for providing thermal conduction while providing electrical isolation.

FIG. 15 shows a corresponding exemplary embodiment. The boiling chamber 80 is surrounded by a filled polymeric structure 10 with a filling material increasing thermal conductivity and providing a tissue contact surface sufficiently large for cryotherapy. The filled polymeric structure may be a polymeric matrix material with short not orientated fiber segments forming a material of increased macroscopically isotropic thermal conduction and a relatively high stiffness comparable to metallic structures. On this boiling chamber 80, ring electrodes 60 are attached of comparable size to standard radio frequency (RF) ablation catheters allowing for identical spatial resolution in ECG recordings compared to RF ablation. For the distal electrode pair, electric wires 69 are shown exemplarily. The thermally conducting tip 10 is connected to a shaft 70 applying any know technique like gluing, screwing or welding. Note that in this embodiment no separation between a thermally conducting and isolating structure is made as due to the small tip size sufficient refrigerant flow can be provided even without a distinct isolating region. However, in some embodiments a separation in a thermally conducting and isolating region may be applied. A pull wire 75 can be foreseen for making the catheter tip deflectable.

In FIG. 16 yet another embodiment is shown with a distinct tip electrode 61 forming the distal closure of the boiling chamber 80. Here, combining electrodes 61 and 62 an even better spatial resolution at the distal tip compared to RF catheters can be obtained. Note that still most of the heat flow to the tissue will be conducted by the electrically isolating boiling chamber 80. In this situation semi-finished parts such as tubes can be used for constructing the cryoapplicator (boiling chamber housing) 10 which may reduce the cost for production. The distal electrode 61 can be fixed in the boiling chamber by any know fixing mechanism such as gluing, screwing, etc.

Alternatively or additionally, a tip forming procedure can be used for bringing the polymer into the desired shape, see FIG. 17, and for providing force fit and leak-proof attachment of the boiling chamber housing 10 with the distal electrode 61. At the proximal end of the boiling chamber polymer welding can be applied for a force fit and leak-proof attachment of boiling chamber 10 and catheter shaft 70. However, also any other known fixation technique can be applied.

Figure 18:
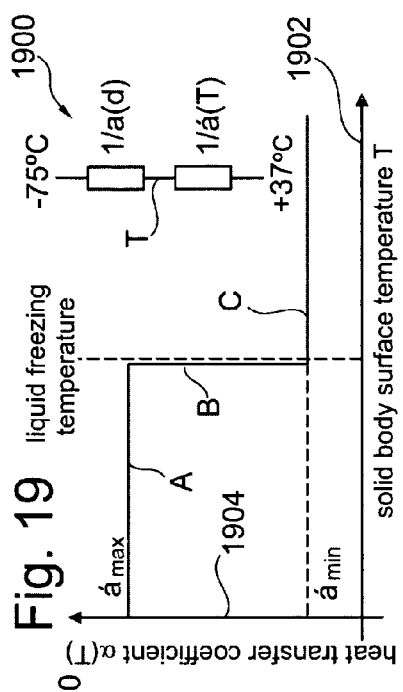
FIG. 18 is a diagram illustrating a dependency between the temperature at an ablation applicator and the time as obtained experimentally and by computer simulation.
Figure 19:
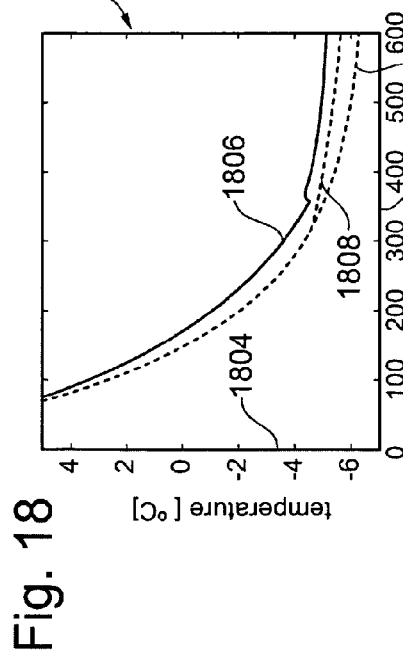
FIG. 19 illustrates the dependency between a heat transfer coefficient and a solid body surface temperature.

FIG. 18 illustrates a diagram 1800 having an abscissa 1802 along which the time is plotted. Along an ordinate 1804 the temperature is plotted. A first curve 1806 relates to measurement data, whereas a second curve 1808 relates to a first computer simulation and a third curve 1810 relates to a second computer simulation FIG. 19 plots a diagram 1900 having an abscissa 1902 along which the solid body surface temperature is plotted. Along an ordinate 1904 a heat transfer coefficient is plotted. The curve shown in diagram 1900 corresponds to the dashed trace 1808 in FIG. 18.

Figure 20:
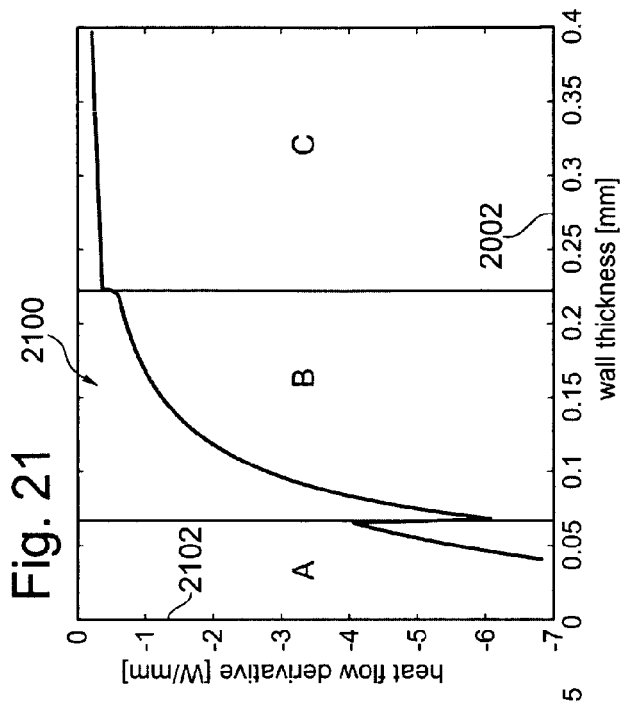
FIG. 20 shows a diagram illustrating the dependency between a calculated heat flow and a wall thickness of an ablation applicator according to an exemplary embodiment of the invention.

FIG. 20 illustrates a diagram 2000 having an abscissa 2002 along with a wall thickness of tubing is plotted. Along an ordinate 2004 a heat flow is plotted. In the diagram 2000, three sections A, B and C are distinguished which can also be seen in FIG. 19.

Figure 21:
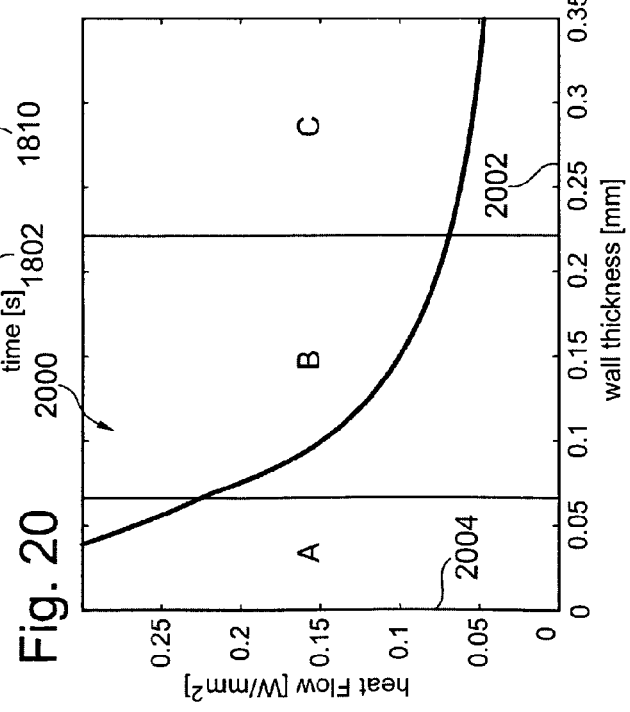
FIG. 21 shows a diagram illustrating the dependency between a derivative of the heat flow and a wall thickness of an ablation applicator according to an exemplary embodiment of the invention.

FIG. 21 illustrates a diagram 2100 which has the same abscissa 2002 as the diagram 2000. Along an ordinate 2102 the derivative of the heat flow is plotted which shows meaningful features particularly at borders between sections A and B and between sections B and C, respectively.

FIG. 18 to FIG. 21 illustrate the model underlying the thermal dimensioning of the thermally isolating region (and conductive region) in the context of embodiments of the present invention. It is assumed that the worst case thermal load imposed on the cryo-applicator is due to blood stream. Dimensioning is based on the assumption that the heat transfer coefficient (a) between a solid body and a liquid increases substantially when the surface temperature of the solid body drops below the freezing temperature of the liquid.

This assumption is supported by experimental data shown in FIG. 18. A metallic surface is cooled in a water bath by a thermoelectric cooler. The measured temperature is indicated by the first curve 1806. A sharp bend can be observed in the measured temperature trace when surface temperature drops by about five degrees below the freezing point of water. This measurement data is compared with two computer simulations, see second and third curves 1808, 1810. In one model (dashed trace, second curve 1808) a step like change of the heat transfer coefficient is assumed at −4.6° C. as indicated in FIG. 19. This model can reproduce the sharp bend in the trace. If in contrast the heat transfer coefficient is assumed to be constant no bend can be observed.

Without being bound to a specific theory the inventors have recognized that the heat transfer to a liquid medium can be reduced by avoiding that the solid body surface temperature drops below the freezing point of the medium. In other words, a thermal isolation is effective when beginning ice formation on the applicator surface is avoided in circulating blood. This can be quantitatively assessed by the following worst case model of the thermal load in the isolating region. Using for example nitrous oxide as refrigerant the temperature in the boiling chamber is determined by the boiling temperature which is close to −90° C. at ambient pressure. Experiments performed by the inventors show that the temperature difference between the boiling chamber and the inner tubing surface can hardly be reduced below 15° C. by improving isolation. Thus, in the worst case model the thermal resistance of the inner surface is described by the smallest expected temperature difference of 15° C. leading to a temperature of −75° C. at the inner surface. As described above a quantitative estimate of the heat transfer property is obtained by $a=\lambda_c/d$. Note that the physical dimension of a is identical to the dimension of the heat transfer coefficient between a solid body and a liquid comparable to water or blood.

Assuming that wall thickness is relatively small compared to the diameter of the tubing an estimate of the heat transfer p (W/m$^2$) across the surface is obtained by $p=\Delta T/(1/a+1/\alpha(T))$.

Here $\alpha(T)$ is the temperature dependent heat transfer coefficient which displays an essentially step like decrease when the surface temperature drops below the freezing temperature of the liquid and $\Delta T$ is the temperature difference between the inner boiling chamber surface and the blood temperature.

FIG. 20 shows the heat transfer computed for polyurethane tubing (0.2 W/mK) of varying wall thickness d assuming a steplike change of the heat transfer coefficient from $\alpha_{min}=2000$ W/m$^2$K to $\alpha_{max}=5000$ W/m$^2$K at a freezing point of $-5°$ C. (data for a physiological saline solution mimicking circulating blood). For a small wall thickness (interval A) the solid body surface temperature is below the freezing point and heat transfer to liquid occurs with $\alpha_{max}$. At the border between intervals A and B the surface temperature reaches the freezing point. In interval B further increasing of wall thickness now reduces the heat flow quickly as the solid body surface temperatures remain constant and the temperature dependent heat transfer coefficient $\alpha(T)$ drops from $\alpha_{max}$ to $\alpha_{min}$. Note that here both a and $\alpha(T)$ decrease as wall thickness increases. At the border between intervals B and C heat transfer coefficient equals $\alpha_{min}$. When wall thickness is further increased (interval C) the heat transfer coefficient remains constant and the reduction of heat transfer is only due to the increase of a as the solid body temperature now increases above the liquid's freezing point. To highlight this observation the derivative of the heat transfer by wall thickness is depicted in FIG. 21. Note that there is a steplike reduction of this derivative when crossing the border from interval B to C. This indicates that any further thickening of the isolation will only result in a modest improvement. Recognizing that space is generally limited in medical applications the interval border to solid body freezing temperatures above the liquid freezing point is a valid indicator for thermal isolation dimensioning. Note that for numbers given above a=1200 W/m$^2$K at the interval border between B and C.

It is believed that the heat transfer coefficient $\alpha_{min}$ depends on local blood flow velocity. Here the investigated value of $\alpha_{min}=2000$ W/m$^2$K is a model for slow blood flow which yields a high value for the heat transfer parameter a at the interval border between B and C. Thus, choosing a $\leq 1200$ W/m$^2$K also for higher blood flow velocities it will be ensured that no ice formation starts at the outer surface as a is sufficiently small compared to $\alpha_{min}$.

In an in-vivo study an elongated transmural lesion of 6 cm length was created with a cryoapplicator of constant wall thickness of 0.11 mm. Here the thermal conductivity of the material was 0.2 W/mK yielding a constant heat transfer parameter of 1820 W/m$^2$K (no distinction between thermally isolating and conducting area). In this experiment the refrigerant flow rate had to be increased by 12% above the maximal tolerable value (increased boiling chamber pressure). Also, this data indicates that choosing a $\leq 1200$ W/m$^2$K in the thermally isolating region will provide sufficient isolation for the creation of elongated lesions at acceptable refrigerant flow rates.

FIG. 22 shows an ablation device 2500 according to an exemplary embodiment of the invention which also includes an ablation applicator 2502. In FIG. 22 it is shown how the ablation device 2500 is inserted into a kidney artery 2510. The ablation applicator 2502 which is configured for cryogenic ablation comprises a tubular body 2504 which defines an inner lumen to which an ablation medium is conductible. The tubular body 2504 may be configured as in any of the embodiments described herein and may or may not have a matrix with particles accommodated therein. The ablation medium may be a cooling agent supplied via a supply element 2506. At an end of the tube 2504 a rounded element 2508 is provided to prevent injury of tissue.

A control mechanism of the ablation applicator 2502 is configured for converting the tubular body 2504 from an elongated operation mode (as one example of a passive operation mode in which no ablation is executed) as shown in FIG. 22 into a spiral operation mode (as one example of an active operation mode in which ablation is or can be executed) shown in FIG. 23.

The control mechanism for performing the conversion between the operation modes of FIG. 22 and FIG. 23 may be an extrinsic mechanism which is provided by a separate member. For instance, a not shown mechanical arrangement may allow performing this conversion. However, alternatively it is also possible that the control mechanism is an intrinsic one. For example, the tubing 2504 may be made of a shape memory material which is configured so that the tube is usually or in a default mode in the elongate state of FIG. 22. However, due to the temperature increase when inserting the tube 2504 into the body may change the configuration so that the configuration is converted from FIG. 22 to FIG. 23.

With the shown embodiment it is possible to ablate tissue of the blood vessel along a helical path of the spirally wound tube 2504 which results in a basically cylindrical ablation area. This is shown in the detailed drawing of FIG. 23. In section 2600 in which the spiral wound tube 2504 is oriented during the ablation procedure, the tissue will be ablated. However, in connected portions 2602, 2604 of the blood vessel 2510 no oblation occurs.

As an alternative to an ablation along a cylindrical ablation area as shown in FIG. 23, it is also possible to ablate tissue simultaneously at different ablation positions being spaced from one another. For example, an ablation applicator may be placed along a defined trajectory into a blood vessel of a kidney so that multiple ablation spots (resulting in punctual lesions) are defined by individual highly thermally conductive surface portions of the ablation applicator. In one subsequent ablation procedure (for instance with one common freeze), all spots may be activated so as to form the multiple ablated tissue portions at the same time.

It should be noted that the term "comprising" does not exclude other elements or steps and the "a" or "an" does not exclude a plurality. Also elements described in association with different embodiments may be combined. It should also be noted that reference signs in the claims shall not be construed as limiting the scope of the claims.

The invention claimed is:
1. An ablation applicator for an ablation device, the ablation applicator comprising:
a tubular body defining an inner lumen to which an ablation medium is conductible;
wherein the tubular body comprises a polymeric matrix accommodating a plurality of particles, said tubular body having a heat transfer parameter greater than approximately 1500 W/m2K at least in a portion of the circumference;
an ablation medium supply line for supplying the ablation medium to the inner lumen, the ablation medium supply line being arranged within the inner lumen and having a number of openings for passing ablation medium from the ablation medium supply line to the inner lumen for thermally contacting the ablation medium with the tubular body; and
a first temperature sensor and a second temperature sensor arranged within the inner lumen,
wherein the first temperature sensor is positioned at one of the openings at an end of the inner lumen, and wherein the second temperature sensor is positioned at another one of the openings at an opposite end of the inner lumen.

2. The ablation applicator according to claim 1, wherein at least a part of the plurality of particles are oriented isotropically in the matrix.

3. The ablation applicator according to claim 1, wherein at least a part of the plurality of particles comprise beads selected from the group consisting of tungsten beads, silver beads, gold beads, barium sulphate beads, and beads made of a contrast agent.

4. The ablation applicator according to claim 3, wherein at least 50% of the beads have a size in a largest dimension in a range between 100 nm and 100 µm.

5. The ablation applicator according to claim 1, wherein at least one of the group consisting of at least a part of the particles, and the matrix comprises or consists of a shape-memory material.

6. The ablation applicator according to claim 1, further comprising a structure of a shape-memory material provided separately from the matrix and being located in the inner lumen.

7. The ablation applicator according to claim 1, wherein the plurality of particles is accommodated in the matrix with a spatially varying composition around a circumference and/or along a longitudinal extension of the tubular body.

8. The ablation applicator according to claim 1, wherein the plurality of particles is accommodated in the matrix so that the tubular body has a circumferentially and/or longitudinally varying thermal conductivity.

9. The ablation applicator according to claim 1, wherein the plurality of particles is accommodated in the matrix so that the tubular body has a thermal conductivity along at least a part of its circumference of more than 0.30 W/(mK).

10. The ablation applicator according to claim 3, wherein a percentage of the beads in the tubular body is in a range between 40 mass % and 70 mass %.

11. The ablation applicator according to claim 1, wherein the tubular body comprises a first section in which a plurality of particles of a first type is accommodated in the matrix, and a second section in which a plurality of particles of a second type is accommodated in the matrix, the first section and the second section being different circumferential sections of the tubular body.

12. The ablation applicator according to claim 11, wherein the tubular body comprises a third section being free of particles and consisting of material of the matrix.

13. The ablation applicator according to claim 11, wherein the particles of the first type are thermally conductive, and the particles of the second type are thermally insulating.

14. The ablation applicator according to claim 1, wherein the tubular body comprises a first section in which a part of the plurality of particles is accommodated in a matrix section of a first type, and a second section in which another part of the plurality of particles is accommodated in a matrix section of a second type.

15. The ablation applicator according to claim 1, wherein at least a part of the particles has a core and a coating at least partially covering the core.

16. The ablation applicator according to claim 1, wherein the tubular body has a closed end formed at least partially by material of the matrix and by at least a part of the particles.

17. The ablation applicator according to claim 16, comprising at least one electrically conductive structure at an exterior surface of the closed end and being connected to the tubular body.

18. The ablation applicator according to claim 1, wherein an outer circular perimeter of the tubular body and a circular perimeter of the inner lumen are eccentric so that a thickness of the tubular body varies along a circumference of the tubular body.

19. The ablation applicator according to claim 1, wherein a wall thickness of the tubular body is smaller than 0.35 mm.

20. The ablation applicator according to claim 1, wherein the openings are arranged with a predetermined spacing in a longitudinal direction of the tubular body, wherein the predetermined spacing is less than 8 mm.

21. The ablation applicator according to claim 20, wherein a cross-sectional area of at least one proximal opening is smaller than a cross-sectional area of at least one distal opening.

22. The ablation applicator according to claim 1, further comprising a shaping structure arranged within the inner lumen and adapted to provide the tubular body with a desired shape, wherein the shaping structure comprises nitinol, wherein the shaping structure comprises an austenite finish temperature below 12° C.

23. An ablation device, the ablation device comprising an ablation catheter comprising an ablation applicator according to claim 1 and being adapted to ablate material of a heart.

24. A method of configuring an ablation applicator for an ablation device in accordance with at least one predefined ablation characteristic, the method comprising:
forming a tubular body defining an inner lumen to which an ablation medium is conductible and comprising a polymeric matrix accommodating a plurality of particles, said tubular body having a heat transfer parameter greater than approximately 1500 W/m2K at least in a portion of the circumference;
selecting the matrix and the particles so as to meet the at least one predefined ablation characteristic by the correspondingly configured ablation applicator;
arranging an ablation medium supply line within the inner lumen for supplying ablation medium to the inner lumen, the ablation medium supply line having a number of openings for passing the ablation medium from the ablation medium supply line to the inner lumen for thermally contacting the ablation medium with the tubular body; and
positioning a first temperature sensor and a second temperature sensor within the inner lumen, wherein the first temperature sensor is positioned at one of openings at an end of the inner lumen, and wherein the second temperature sensor is positioned at another one of the openings at an opposite end of the inner lumen.

25. An ablation method, comprising:
conducting an ablation medium to an inner lumen defined within a tubular body which comprises a polymeric matrix accommodating a plurality of particles, said tubular body having a heat transfer parameter smaller than 1200 W/m2K at least in a portion of the circumference, the ablation medium being conducted to the inner lumen by an ablation medium supply line arranged within the inner lumen and having a number of openings for passing the ablation medium from the ablation medium supply line to the inner lumen for thermally contacting the ablation medium with the tubular body;

detecting a first temperature of the ablation medium using a first temperature sensor positioned within the inner lumen at one of the openings at an end of the inner lumen;

detecting a second temperature of the ablation medium using a second temperature sensor positioned within the inner lumen at another one of the openings at an opposite end of the inner lumen; and contacting the ablating material with an external surface of the tubular body.

26. A cryoapplicator tubing made from a polymer being filled with particles in a first section and being unfilled in another second section, where at least in one quarter of a circumference of the cryoapplicator tubing, a heat transfer parameter is larger than 1500 W/m2K and at least in one other quarter of the circumference the heat transfer parameter is smaller than 1200 W/m2K, and wherein the heat transfer parameter is a ratio between thermal conductivity and wall thickness of the cryoapplicator tubing.

27. An ablation applicator for an ablation device for ablating tissue of a blood vessel the ablation applicator comprising:

a tubular body, defining an inner lumen to which an ablation medium is conductible, the tubular body comprising a polymeric tubing, said tubing having a heat transfer parameter greater than approximately 1500 W/m2K at least in a portion of the circumference;

a control mechanism configured for converting the tubular body between a passive operation mode for inserting the ablation applicator into the blood vessel and an active operation mode for ablating tissue of the blood vessel;

an ablation medium supply line for supplying the ablation medium to the inner lumen, the ablation medium supply line being arranged within the inner lumen and having a number of openings for passing the ablation medium from the ablation medium supply line to the inner lumen for thermally contacting the ablation medium with the tubular body; and a first temperature sensor and a second temperature sensor arranged within the inner lumen, wherein the first temperature sensor is positioned at one of the openings at an end of the inner lumen, and wherein the second temperature sensor is positioned at another one of the openings at an opposite end of the inner lumen.

28. The ablation applicator of claim 27, wherein a size of an opening at an end of the inner lumen is smaller than a size of another opening at the opposite end of the inner lumen.

* * * * *